(12) United States Patent
Shih et al.

(10) Patent No.: US 9,448,223 B2
(45) Date of Patent: Sep. 20, 2016

(54) IMPEDANCE-BASED SENSING OF ADHERENT CELLS ON A DIGITAL MICROFLUIDIC DEVICE

(71) Applicant: The Governing Council of The University of Toronto, Toronto (CA)

(72) Inventors: Steve Chao-Chung Shih, Toronto (CA); Irena Barbulovic-Nad, Toronto (CA); Aaron Wheeler, Toronto (CA)

(73) Assignee: The Governing Council of the University of Toronto, Ontario (CA)

( * ) Notice: Subject to any disclaimer, the term of this patent is extended or adjusted under 35 U.S.C. 154(b) by 0 days.

(21) Appl. No.: 14/063,366

(22) Filed: Oct. 25, 2013

(65) Prior Publication Data

US 2014/0199719 A1     Jul. 17, 2014

Related U.S. Application Data

(60) Provisional application No. 61/752,298, filed on Jan. 14, 2013.

(51) Int. Cl.
*C12M 1/34* (2006.01)
*C12M 3/00* (2006.01)
(Continued)

(52) U.S. Cl.
CPC ..... *G01N 33/4836* (2013.01); *B01L 3/502792* (2013.01); *C12M 23/16* (2013.01); *C12M 25/01* (2013.01); *C12M 25/08* (2013.01); *C12M 41/36* (2013.01)

(58) Field of Classification Search
CPC ....... C12Q 1/02; C12M 23/16; C12M 25/01; C12M 25/08; C12M 33/00; C12M 41/00; C12M 41/36; B01L 2200/027; B01L 2200/0605; B01L 2300/0819; B01L 2300/0867; B01L 2300/089; B01L 2400/0427; B01L 2400/0688; B01N 33/54386; B01N 33/4836
See application file for complete search history.

(56) References Cited

U.S. PATENT DOCUMENTS

2004/0058450 A1\* 3/2004 Pamula et al. ................ 436/150
2009/0203063 A1   8/2009 Wheeler et al.
(Continued)

FOREIGN PATENT DOCUMENTS

CN   103170383       5/2015
WO   2008101194 A2   8/2008
(Continued)

OTHER PUBLICATIONS

Abdelgawad, M., Wheeler, A.R., 2009. Adv Mater 21, 920-925.
(Continued)

*Primary Examiner* — Michael Hobbs
(74) *Attorney, Agent, or Firm* — Quarles & Brady, LLP

(57) ABSTRACT

Devices and methods are provided for measuring, on a digital microfluidic platform, electrical signals associated with the impedance of adherent cells. In one embodiment, a sub-droplet of cell culture media containing adherent cells is passively dispensed at a pre-selected electrode location where a local hydrophilic surface region is provided, and adherent cells are attached to the local hydrophilic surface region. The cell culture media sub-droplet is replaced with a sub-droplet of a low-conductivity medium in a passive dispensing step, retaining the attached adherent cells. An AC voltage with a suitable frequency is applied between electrodes of the device and a signal associated with the impedance of the adherent cells is obtained. One of the electrodes to which the AC voltage is applied may be a dedicated sensing electrode. The local thickness of a dielectric layer coating the pre-selected electrode may be reduced to increase the detection sensitivity of the device.

21 Claims, 15 Drawing Sheets

(51) Int. Cl.
  *G01N 33/483* (2006.01)
  *B01L 3/00* (2006.01)
  *C12M 1/12* (2006.01)
  *C12M 3/06* (2006.01)

(56) References Cited

U.S. PATENT DOCUMENTS

| | | |
|---|---|---|
| 2009/0218223 A1 | 9/2009 | Manaresi et al. |
| 2010/0311599 A1 | 12/2010 | Wheeler et al. |
| 2012/0003687 A1 | 1/2012 | Toner et al. |
| 2012/0006684 A1 | 1/2012 | Hadwen et al. |
| 2012/0007608 A1 | 1/2012 | Hadwen et al. |
| 2012/0044299 A1 | 2/2012 | Winger |
| 2012/0106238 A1 | 5/2012 | John et al. |
| 2013/0143312 A1 | 6/2013 | Wheeler et al. |

FOREIGN PATENT DOCUMENTS

| | | |
|---|---|---|
| WO | 2010091334 | 8/2010 |
| WO | 2012037308 A2 | 3/2012 |

OTHER PUBLICATIONS

Abdolahad, M., Taghinejad, M., Taghinejad, H., Janmaleki, M., Mohajerzadeh, S., 2012. Lab on a Chip 12, 1183-1190.
Abramoff, M.D., Magalhaes, P.J., Ram, S.J., 2004. Biophotonics International 11, 36-42.
Adams, A.A., Okagbare, P.I., Feng, J., Hupert, M.L., Patterson, D., Gottert, J., McCarley, R.L., Nikitopoulos, D., Murphy, M.C., Soper, S.A., 2008. Journal of the American Chemical Society 130, 8633-8641.
Asphahani, F., Thein, M., Veiseh, O., Edmondson, D., Kosai, R., Veiseh, M., Xu, J., Zhang, M., 2008. Biosens Bioelectron 23, 1307-1313.
Ayliffe, H.E., Frazier, A.B., 1999. Journal of Microelectromechanical Systems 8, 50-57.
Barbulovic-Nad, I., Au, S.H., Wheeler, A.R., 2010. Lab on a Chip 10, 1536-1542.
Barbulovic-Nad, I., Yang, H., Park, P.S., Wheeler, A.R., 2008. Lab on a Chip 8, 519-526.
Boeck, G., 2001. International Review of Cytology—a Survey of Cell Biology 204, 239-298.
Bogojevic, D., Chamberlain, M.D., Barbulovic-Nad, I., Wheeler, A.R., 2012. Lab on a Chip 12, 627-634.
Brischwein, M., Herrmann, S., Vonau, W., Berthold, F., Grothe, H., Motrescu, E.R., Wolf, B., 2006. Lab on a Chip 6, 819-822.
Chen, J., Zheng, Y., Tan, Q., Zhang, Y.L., Li, J., Geddie, W.R., Jewett, M.A., Sun, Y., 2011. Biomicrofluidics 5, 14113.
Cheng, X, Liu, Y.S., Irimia, D., Demirci, U., Yang, L., Zamir, L., Rodriguez, W.R., Toner, M., Bashir, R., 2007. Lab on a Chip 7, 746-755.
Cho, S.K., Moon, H.J., Kim, C.J., 2003. Journal of Microelectromechanical Systems 12, 70-80.
Cho, Y.H., Yamamoto, T., Sakai, Y., Fujii, T., Kim, B., 2006. Journal of Microelectromechanical Systems 15, 287-295.
Curtis, T.M., Widder, M.W., Brennan, L.M., Schwager, S.J., van der Schalie, W.H., Fey, J., Salazar, N., 2009. Lab on a Chip 9, 2176-2183.
DePaola, N., Phelps, J.E., Florez, L., Keese, C.R., Minnear, F.L., Giaever, I., Vincent, P., 2001. Ann Biomed Eng 29, 648-656.
Dharmasiri, U., Balamurugan, S., Adams, P.I., Obubuafo, A., Soper, S.A., 2009. Electrophoresis 30, 3289-3300.
Dharmasiri, U., Njoroge, S.K., Witek, M.A., Adebiyi, M.G., Kamande, J.W., Hupert, M.L., Barany, F., Soper, S.A., 2011. Analytical Chemistry 83, 2301-2309.
Dive, C., Gregory, C.D., Phipps, D.J., Evans, D.L., Milner, A.E., Wyllie, A.H., 1992. Biochimica et Biophysica Acta 1133, 275-285.
Eydelnant, I.A., Uddayasankar, U., Li, B., Liao, M.W., Wheeler, A.R., 2012. Lab on a Chip 12, 750-757.
Fan, S.K., Huang, P.W., Wang, T.T., Peng, Y.H., 2008. Lab on a Chip 8, 1325-1331.
Fiddes, L.K., Luk, V.N., Au, S.H., Ng, A.H.C., Luk, V.M., Kumacheva, E., Wheeler, A.R., 2012. Biomicrofluidics 6, 014112.
Gawad, S., Cheung, K., Seger, U., Bertsch, A., Renaud, P., 2004. Lab on a Chip 4, 241-251.
Giaever, I., Keese, C.R., 1991. Proc Natl Acad Sci U S A 88, 7896-7900.
Giaever, I., Keese, C.R., 1993. Nature 366, 591-592.
Gray, D.S., Tan, J.L., Voldman, J., Chen, C.S., 2004. Biosens Bioelectron 19, 1765-1774.
Hadwen, B., Broder, G.R., Morganti, D., Jacobs, A., Brown, C., Hector, J.R., Kubota, Y., Morgan, H., 2012. Lab on a Chip 12, 3305-3313.
Han, A., Frazier, A.B., 2006. Lab on a Chip 6, 1412-1414.
Han, A., Yang, L., Frazier, A.B., 2007. Clinical Cancer Research 13, 139-143.
Han, K.H., Han, A., Frazier, A.B., 2006. Biosens Bioelectron 21, 1907-1914.
Holmes, D., Pettigrew, D., Reccius, C.H., Gwyer, J.D., van Berkel, C., Holloway, J., Davies, D.E., Morgan, H., 2009. Lab Chip 9, 2881-2889.
Ikeda, M., Kohno, M., Takeda, T., 1995. Hypertension 26, 401-405.
James, C.D., Reuel, N., Lee, E.S., Davalos, R.V., Mani, S.S., Carroll-Portillo, A., Rebeil, R., Martino, A., Apblett, C.A., 2008. Biosens Bioelectron 23, 845-851.
Jang, L.S., Wang, M.H., 2007. Biomedical Microdevices 9, 737-743.
Keese, C.R., Bhawe, K., Wegener, J., Giaever, I., 2002. Biotechniques 33, 842-844.
Keese, C.R., Wegener, J., Walker, S.R., Giaever, I., 2004. Proc Natl Acad Sci U S A 101, 1554-1559.
Kunas, K.T., Papoutsakis, E.T., 2009. Biotechnology and bioengineering 102, 980-987; discussion 977-989.
Lippincott-Schwartz, J., 2011. Annu Rev Biochem 80, 327-332.
Lo, C.M., Keese, C.R., Giaever, I., 1995. Biophys J 69, 2800-2807.
Lundien, M.C., Mohammed, K.A., Nasreen, N., Tepper, R.S., Hardwick, J.A., Sanders, K.L., Van Horn, R.D., Antony, V.B., 2002. J Clin Immunol 22, 144-152.
Mengual Gomez, D.L., Belaich, M.N., Rodriguez, V.A., Ghiringhelli, P.D., 2010. BMC Biotechnol 10, 68.
Mishra, N.N., Retterer, S., Zieziulewicz, T.J., Isaacson, M., Szarowski, D., Mousseau, D.E., Lawrence, D.A., Turner, J.N., 2005. Biosens Bioelectron 21, 696-704.
Morgan, H., Sun, T., Holmes, D., Gawad, S., Green, N.G., 2007. J. Phys. D: Appl. Phys. 40, 61-70.
Otto, A.M., Brischwein, M., Niendorf, A., Henning, T., Motrescu, E., Wolf, B., 2003. Cancer Detect Prev 27, 291-296.
Rumenapp, C., Remm, M., Wolf, B., Gleich, B., 2009. Biosens Bioelectron 24, 2915-2919.
Shah, G.J., Ohta, A.T., Chiou, E.P., Wu, M.C., Kim, C.J., 2009. Lab on a Chip 9, 1732-1739.
Shah, G.J., Veale, J.L., Korin, Y., Reed, E.F., Gritsch, H.A., Kim, C.J., 2010. Biomicrofluidics 4, 44106.
Shih, S.C.C., Fobel, R., Kumar, P., Wheeler, A.R., 2011. Lab on a Chip 11, 535-540.
Shih, S.C.C., Yang, H., Jebrail, M.J., Fobel, R., McIntosh, N., Al-Dirbashi, O.Y., Chakraborty, P., Wheeler, A.R., 2012. Analytical Chemistry 84, 3731-3738.
Sohn, L.L., Saleh, O.A., Facer, G.R., Beavis, A.J., Allan, R.S., Notterman, D.A., 2000. Proc Natl Acad Sci U S A 97, 10687-10690.
Srigunapalan, S., Eydelnant, I.A., Simmons, C.A., Wheeler, A.R., 2012. Lab on a Chip 12, 369-375.
Stolwijk, J.A., Hartmann, C., Balani, P., Albermann, S., Keese, C.R., Giaever, I., Wegener, J., 2011. Biosens Bioelectron 26, 4720-4727.
Sun, T., Morgan, H., 2010. Microfluid Nanofluid 8, 423-443.
Sun, T., Swindle, E.J., Collins, J.E., Holloway, J.A., Davies, D.E., Morgan, H., 2010. Lab on a Chip 10, 1611-1617.
Sun, T., van Berkel, C., Green, N.G., Morgan, H., 2009. Microfluid Nanofluid 6, 179-187.
Taff, B.M., Voldman, J., 2005. Analytical Chemistry 77, 7976-7983.

(56) References Cited

OTHER PUBLICATIONS

Thein, M., Asphahani, F., Cheng, A., Buckmaster, R., Zhang, M., Xu, J., 2010. Biosens Bioelectron 25, 1963-1969.
Tiruppathi, C., Malik, A.B., Del Vecchio, P.J., Keese, C.R., Giaever, I., 1992. Proc Natl Acad Sci U S A 89, 7919-7923.
Vergauwe, N., Witters, D., Ceyssens, F., Vermeir, S., Verbruggen, B., Puers, R., Lammertyn, J., 2011. Journal of Micromechanics and Microengineering 21.
Wang, L., Zhu, J., Deng, C., Xing, W.L., Cheng, J., 2008. Lab on a Chip 8, 872-878.
Wegener, J., Sieber, M., Galla, H.J., 1996. J Biochem Biophys Methods 32, 151-170.
Weinlich, M., Heydasch, U., Mooren, F., Starlinger, M., 1998. Res Exp Med (Berl) 198, 73-82.
Wheeler, A.R., 2008. Science 322, 539-540.
Witters, D., Vergauwe, N., Vermeir, S., Ceyssens, F., Liekens, S., Puers, R., Lammertyn, J., 2011. Lab on a Chip 11, 2790-2794.
Zudaire, E., Cuesta, N., Murty, V., Woodson, K., Adams, L., Gonzalez, N., Martinez, A., Narayan, G., Kirsch, I., Franklin, W., Hirsch, F., Birrer, M., Cuttitta, F., 2008. Journal of Clinical Investigation 118, 640-650.
Webpage Title: xCELLigence System Web Address: http://web.archive.org/web/20120615141114/http:/www.roche-diagnostics.co.in/Products/Pages/xcelligencesystem.aspx Date of printing from website: Jul. 18, 2012.
Webpage title: Applied BioPhysics Quantifying Cell Behavoir Web address: http://www.biophysics.com/ecis-theory.php Date of printing from website: Feb. 3, 2014.
Ren et al., Automated on-chip droplet dispensing with volume control by electro-wetting actuation and capacitance metering, Sensors and Actuators B 98 (2004) 319-327.
Gong et al., All-electronic droplet generation on-chip with real-time feedback control for EWOD digital microfluidics, Lab Chip, 2008, 8, 898-906.

\* cited by examiner

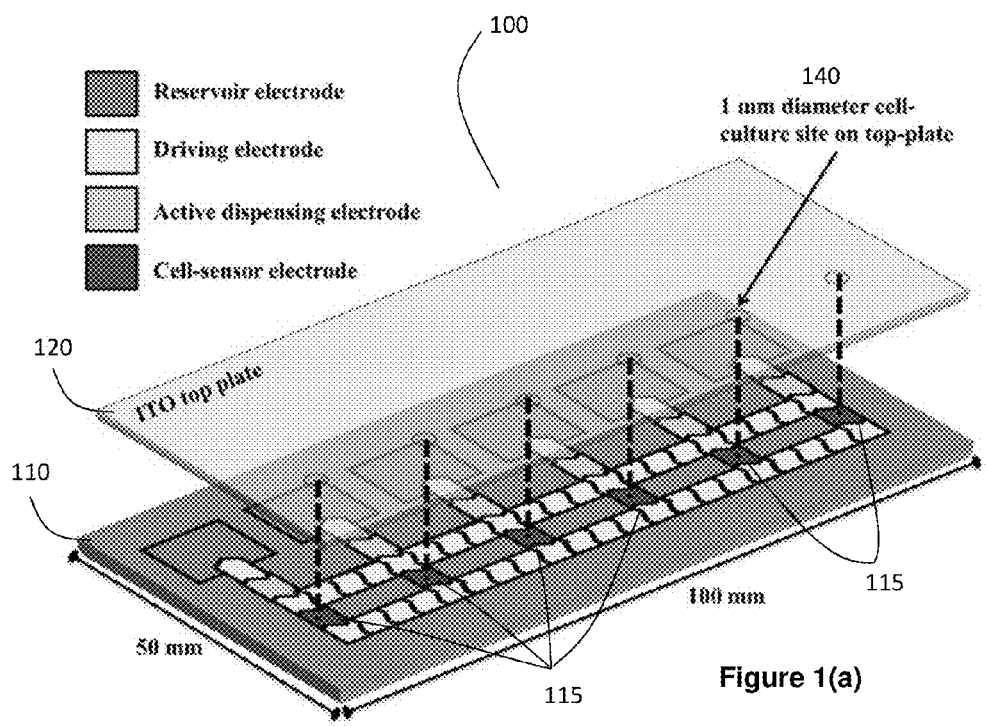
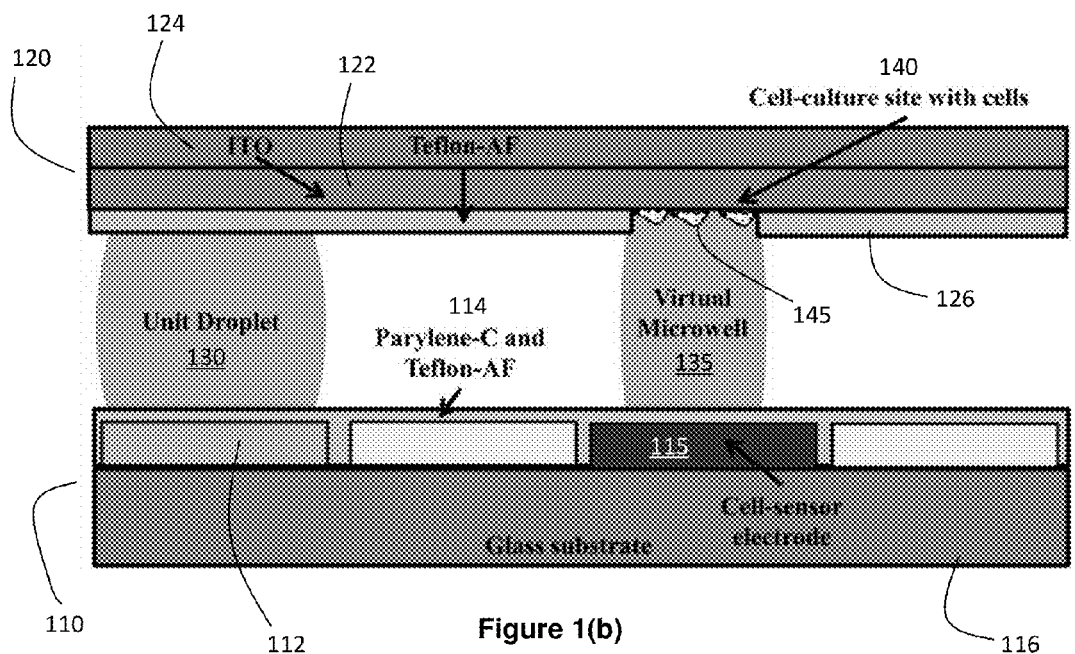
Figure 1(a)
Figure 1(b)

| Item | Circuit Element | Value | Reference or measured | Equation and Parameters |
|---|---|---|---|---|
| Element 1: insulator | $C_i$ | 10.4 pF | N/A | Eq. 2; $\varepsilon_r = 3.0$; $t = 2$ μm; $A = 0.785$ mm$^2$ |
| Element 2: bulk liquid | $R_{liq\_bulk}$ | cell media: 400 Ω | measured | N/A |
| | | sucrose: 1.8 MΩ | measured | N/A |
| | $C_{liq\_bulk}$ | cell media: ~0 pF | N/A | N/A |
| | | sucrose: 19.5 pF | measured | N/A |
| Element 3: interface | $C_{mem}$ | 0.785 pF·cell$^{-1}$ | (Morgan et al. 2007; Sun and Morgan 2010) | N/A |
| | $R_{cyto}$ | 212 kΩ·cell$^{-1}$ | (Morgan et al. 2007; Sun and Morgan 2010) | Eq. 1; $\rho = 1.67$ Ω·m; $t = 10$ μm; $A = 7.85 \times 10^{-5}$ mm$^2$ |
| | $R_{liq\_int}$ | cell media: 22.9/26.7** Ω | N/A | Eq. 1; $\rho = 1.74$ Ω·m*; $t = 10$ μm; $A = 0.785$ mm$^2$ - $A_c$ |
| | | sucrose: 103/121** kΩ | N/A | Eq. 1; $\rho = 7850$ Ω·m*; $t = 10$ μm; $A = 0.785$ mm$^2$ - $A_c$ |
| | $C_{liq\_int}$ | cell media: ~0 pF | N/A | N/A |
| | | sucrose: 54.6/46.1** pF | N/A | Eq. 2; $\varepsilon_r = 80$; $t = 10$ μm; $A = 0.785$ mm$^2$ - $A_c$ |
| Element 4: meas. circuit | $R_{pot}$ | 12 kΩ | N/A | N/A |
| | $C_{op}$ | 20 pF | N/A | N/A |

* $\rho$ extrapolated from measured $R_{liq\_bulk}$
** Values for low and high cell density

Figure 7

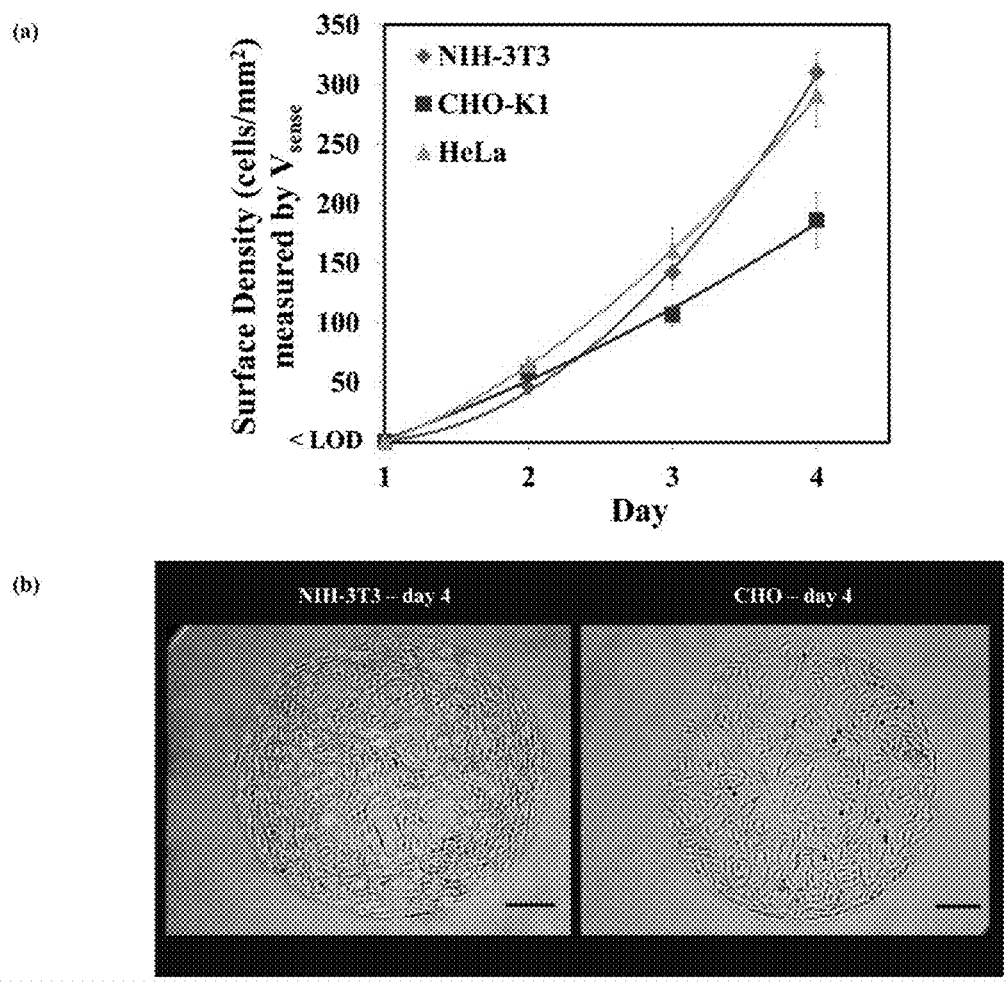
Figures 13(a)-(b)

(a)
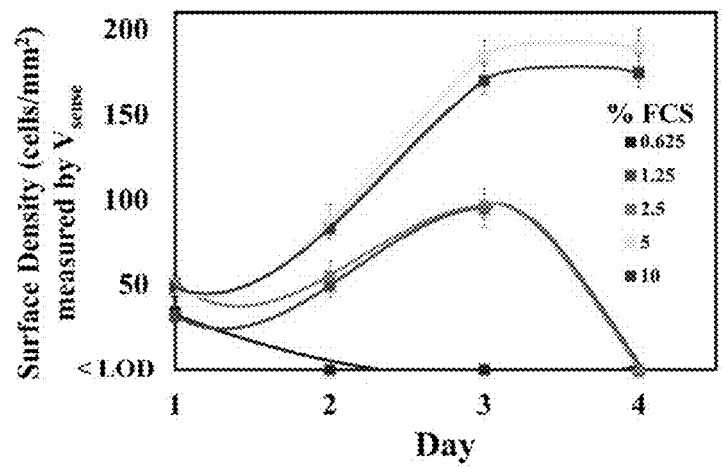
(b)
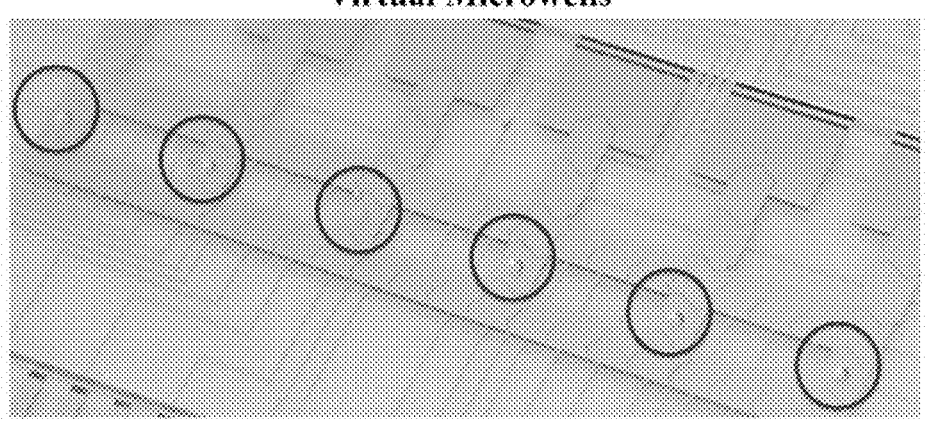
Figures 14(a)-(b)

IMPEDANCE-BASED SENSING OF ADHERENT CELLS ON A DIGITAL MICROFLUIDIC DEVICE

CROSS-REFERENCE TO RELATED APPLICATION

This application claims priority to U.S. Provisional Application No. 61/752,298, titled "IMPEDANCE-BASED SENSING OF ADHERENT CELLS ON A DIGITAL MICROFLUIDIC DEVICE" and filed on Jan. 14, 2013, the entire contents of which is incorporated herein by reference.

BACKGROUND

The most common techniques for studying cell populations are flow cytometry and fluorescence microscopy. Flow cytometry is particularly powerful in that it affords the ability to rapidly evaluate large numbers of cells at the single-cell level. Unfortunately, flow cytometry is limited in that cells must be in suspension for analysis, which often requires enzymatic stripping of adherent cells from the surface they are cultured on. Fluorescence microscopy is thus a useful alternative, as it facilitates the evaluation of adherent cells in situ. But analysis by microscopy also causes significant perturbation through the loading of high concentrations of fluorescent dyes, and (in many cases) through the toxic process of permeabilization and fixation.

An alternative to flow cytometry and fluorescence microscopy for analyzing the behavior of adherent cells is impedance analysis. In this method, a layer of cells is grown on the surface of a micropatterned electrode and is exposed to low-magnitude AC voltage. Current then flows between the cells such that the impedance is correlated with cell number, and capacitatively couples through the cells such that the impedance is correlated with cell type and state. This method is growing in popularity, as it enables real-time analysis of cells in culture without the need for enzymatic stripping, fluorescent dyes, fixatives, or other perturbations.

A limitation for most cell impedance measurement systems relative to flow cytometry and microscopy is throughput. Typically, cell impedance analysis systems are integrated in multiwell plate format; e.g., the Applied Biophysics ECIS® system. In laboratories lacking robotic dispensers and aspirators, this forms a practical limit to the throughput that is achievable. Moreover, such techniques require significant cell and reagent use, making them cost-prohibitive for many researchers.

SUMMARY

Devices and methods are provided for measuring, on a digital microfluidic platform, electrical signals associated with the impedance of adherent cells. In one embodiment, a sub-droplet of cell culture media containing adherent cells is passively dispensed at a pre-selected electrode location where a local hydrophilic surface region is provided, and adherent cells are attached to the local hydrophilic surface region. The cell culture media sub-droplet is replaced with a sub-droplet of a low-conductivity medium in a passive dispensing step, retaining the attached adherent cells. An AC voltage with a suitable frequency is applied between electrodes of the device and a signal associated with the impedance of the adherent cells is obtained. One of the electrodes to which the AC voltage is applied may be a dedicated sensing electrode. The local thickness of a dielectric layer coating the pre-selected electrode may be reduced to increase the detection sensitivity of the device.

Accordingly, in one aspect, there is provided a method of measuring an electrical signal associated with the presence of adherent cells on a digital microfluidic device;

the digital microfluidic device comprising:
a first plate comprising a first insulating substrate, an array of discrete electrodes formed on the first insulating substrate and a first dielectric layer provided on the discrete electrodes, wherein a surface of the first dielectric layer is hydrophobic;
a second plate comprising a second insulating substrate at least one reference electrode formed on the second insulating substrate, and a second dielectric layer provided on the reference electrode, wherein a surface of the second dielectric layer is hydrophobic, wherein the second plate is provided in a spaced relationship relative to the first plate;
wherein the digital microfluidic device includes a droplet of cell culture media located between the first plate and the second plate, the droplet of cell culture medium contacting a locally hydrophilic surface region that is proximal to a pre-selected discrete electrode of the array of discrete electrodes, wherein the locally hydrophilic surface region is comprises adherent cells attached thereto;

the method comprising:
electrically actuating the digital microfluidic device to transport a droplet of low-conductivity medium to the pre-selected discrete electrode, wherein the electrical conductivity of the low-conductivity medium is lower than the electrical conductivity of the cell culture medium;
electrically actuating the digital microfluidic device to passively dispense a sub-droplet of the low-conductivity medium, thereby displacing the droplet of cell culture medium; and
applying an AC voltage between the pre-selected discrete electrode and the reference electrode and measuring an electrical signal associated with the impedance of the adherent cells.

In another aspect, there is provided a digital microfluidic device comprising:
a first plate comprising:
a first insulating substrate;
an array of discrete electrodes formed on said first insulating substrate;
a first dielectric layer provided on said discrete electrodes, wherein a surface of said first dielectric layer is hydrophobic;
a second plate comprising:
a second insulating substrate;
at least one reference electrode formed on said second insulating substrate; and
a second dielectric layer provided on said reference electrode, wherein a surface of said second dielectric layer is hydrophobic;
wherein said second plate is provided in a spaced relationship relative to said first plate, such that a droplet contacting said first plate and said second plate is transportable among locations associated with said discrete electrodes under application of a suitable bias between said discrete electrodes and said reference electrode;
wherein at least one of said first plate and said second plate comprises a locally hydrophilic surface region that is proximal to a pre-selected discrete electrode of said array of discrete electrodes, and wherein said locally hydrophilic surface region is configured for attachment of adherent cells; and wherein at least one of said first dielectric layer and said second dielectric layer has a locally reduced thickness over an area that is proximal to said pre-selected discrete electrode, such that an electrical signal associated with an impedance of adherent cells attached to said locally hydrophilic surface region is measurable with a local increase in sensitivity.

In another aspect, there is provided a digital microfluidic device comprising:
a first plate comprising:
a first insulating substrate;
an array of discrete electrodes formed on said first insulating substrate;
a first dielectric layer provided on said discrete electrodes, wherein a surface of said first dielectric layer is hydrophobic;
a second plate comprising:
a second insulating substrate;
at least one reference electrode formed on said second insulating substrate; and
a second dielectric layer provided on said reference electrode, wherein a surface of said second dielectric layer is hydrophobic;
wherein said second plate is provided in a spaced relationship relative to said first plate, such that a droplet contacting said first plate and said second plate is transportable among locations associated with said discrete electrodes under application of a suitable bias between said discrete electrodes and said reference electrode;
wherein at least one of said first plate and said second plate comprises a locally hydrophilic surface region that is proximal to a pre-selected discrete electrode of said array of discrete electrodes, wherein said locally hydrophilic surface region is configured for attachment of adherent cells; and
wherein at least one of said first plate and said second plate comprises a sensing electrode that is proximal to said locally hydrophilic surface region;
wherein a droplet is transportable to said locally hydrophilic surface region based on the application of a voltage between said pre-selected discrete electrode and said reference electrode, and wherein an electrical signal associated with an impedance of adherent cells attached to said locally hydrophilic surface region is measurable based on another voltage applied between said sensing electrode and one of said discrete electrode and said reference electrode.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1(a) and 1(b) show an example digital microfluidic device for cell culture and impedance sensing. In FIG. 1(a), an isometric view of the device is shown. The bottom plate bears 66 electrodes, and the top-plate has six patterned 1 mm diameter cell-culture sites (produced by locally exposing the underlying ITO layer). FIG. 1(b) shows a side view of the digital microfluidic device. Unit droplets (~1 µL) cover the area over a single driving electrode. Virtual microwells (~0.2 µL) cover the area over a single cell culture site.

In FIG. 4(a), the simulated curves have identical values; a slight artificial offset was added to the dark grey curve to show that there are two curves.

FIG. 7 is a table showing the model circuit values used in LTSPICE simulations.

In FIG. 12(a), images show NIH-3T3 cells seeded at three different volumetric densities ($0.5 \times 10^6$, $1.0 \times 10^6$, and $2.0 \times 10^6$ cells/mL) in virtual microwells. Scale bars are 10 µm, and the surface densities are listed under each picture. FIG. 12(b) plots $V_{sense}$ as a function of surface density for NIH-3T3 (diamonds), HeLa (triangles), and CHO-K1 (squares) cells. The inset shows the same data plotted as a function of the area occupied by the cells. Error bars represent ±1 S.D.

FIGS. 13(a)-13(b) show results from proliferation assays. FIG. 13(a) is a graph plotting surface density measured by impedance as a function of time for NIH-3T3 (diamonds), CHO-K1 (squares), and HeLa (triangles) cultured for four days. Curves were added to guide the eye, and error bars represent ±1 S.D. FIG. 13(b) shows images of NIH-3T3 (left) and CHO-K1 (right) cells cultured in virtual microwells for four days confirming the differences in proliferation rates. Scale bars are 10 µm.

FIGS. 14(a)-14(b) show results from serum screening assays. FIG. 14(a) plots growth curves for NIH-3T3 cells cultured in virtual microwells of media containing 0.63% (squares), 1.25% (squares), 2.5% (squares), 5% (squares), and 10% (squares) fetal calf serum. Curves were added to guide the eye, and error bars represent ±1 S.D. FIG. 14(b) is an image showing six virtual microwells containing cells on a device.

DETAILED DESCRIPTION

Figure 2:
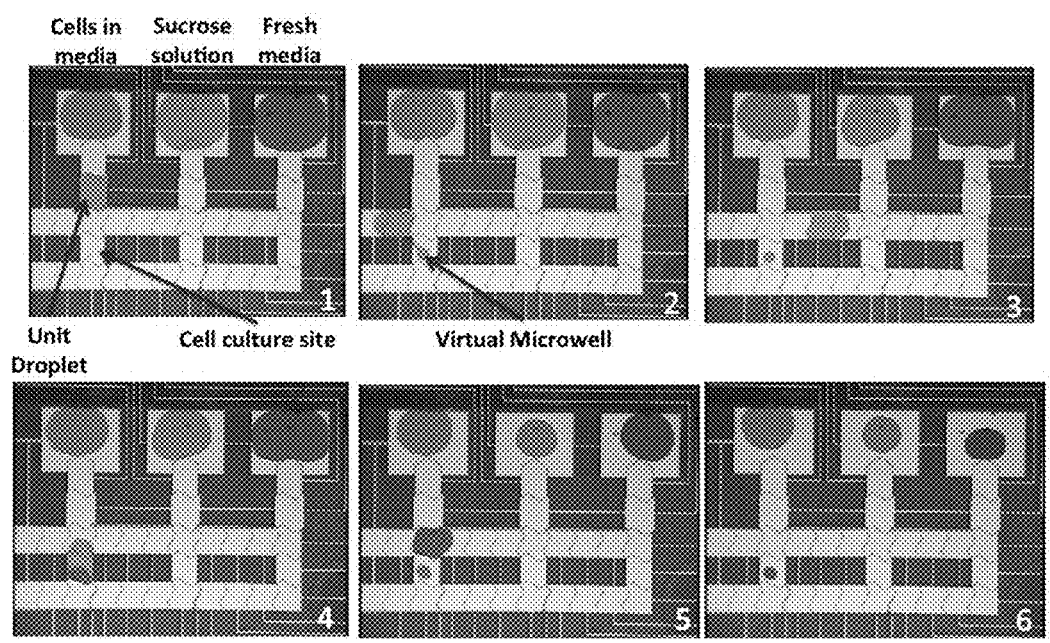
FIG. 2 shows frames from a movie depicting a multistep experiment that illustrates passive dispensing with a virtual microwell on a digital microfluidic platform. In frames 1 and 2, a virtual microwell containing cells is formed. After incubation, in frames 3 and 4, the contents of the virtual microwell are exchanged with a sucrose suspension. Finally, in frames 5 and 6, the contents of the virtual microwell are exchanged with fresh media. Colored dye was added to aid in visualization.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

FIGS. 1(a) and (b) illustrate an example digital microfluidic device 100 that is suitable for impedance detection of adherent cells. The example device is a two-plate digital microfluidic platform, formed from bottom plate 110 and top plate 120. Bottom plate 110 includes discrete electrodes 112 formed on an electrically insulating substrate 116. Electrodes 112 are coated with a dielectric layer having a hydrophobic surface. The plates are separated, for example, by one or more dielectric spacers (not shown), to form an inner channel for supporting and transporting droplets 130. As shown in the Figure, the dielectric layer may be formed, for example, from Parylene and Teflon®AF.

Top plate 120 includes reference electrode layer 122, which is formed on, and supported by, electrically insulating substrate 124. As shown in the Figure, reference electrode layer 122 may be a transparent conductive layer formed from a material such as ITO. Reference electrode layer 122 is covered by dielectric layer 126. Although the example embodiment shown in FIG. 1 includes a single reference electrode on the top plate, it is to be understood that multiple reference electrodes may be included. For example, one reference electrode can be provided for each discrete electrode in the bottom plate. It is also to be understood that the orientation of the "top" and "bottom" plates may be reversed, such that the bottom plate includes one or more reference electrodes, and the top plate includes the array of discrete electrodes.

As illustrated in FIG. 1(b), locally hydrophilic surface regions 140 are patterned on the device surface to serve as sites for cell seeding, spreading, and proliferation, and, according to the present disclosure, measurement, characterization, enumeration, and/or detection via electrical measurements associated with impedance. In addition to being useful for attaching and growing adherent cells 145, these hydrophilic sites also enable a fluidic phenomenon called passive dispensing, which occurs when a unit droplet 130 (i.e., a droplet that covers the space over a single driving electrode) is translated across a hydrophilic site. This results in spontaneous formation of a sub-droplet, shown in FIG. 1(b) at 135, and such sites may also be referred to as virtual microwells.

As shown in FIG. 1(b), locally hydrophilic surface region 140 is formed proximal to a pre-selected discrete electrode 115, such that adherent cells 145 are attached at a location that enables impedance sensing based on the measurement of electrical signals while applying a voltage between pre-selected electrode 115 and reference electrode 122. According to the present example implementation, discrete driving electrode 115 (six of which are shown in FIG. 1(a), illustrating a multiplexed format) serves a dual purpose, acting as an electrode that is actuated for the translation of droplets (and the passive dispensing of sub-droplets), and also acting as a sensor electrode for impedance-based electrical measurements. In other embodiments described below, a separate, dedicated sensing electrode may be provided for the latter purpose.

Although FIGS. 1(a) and 1(b) show the locally hydrophilic surface regions 140 as being formed in the top plate, it is to be understood that they may be provided in any one or more of the top and bottom plates. For example, in one embodiment, a locally hydrophilic region may be formed on the surface of the bottom plate.

Accordingly, the locally hydrophilic surface regions 140, shown in FIGS. 1(a) and (b), may be employed for the passive dispensing of a droplet containing adherent cells, and the subsequent local attachment of adherent cells within the droplet to the hydrophilic surface. In the example embodiment shown, top plate 120 has six patterned 1 mm diameter cell-culture sites (formed by exposing local regions of the ITO layer), which are configured for the passive dispensing of sub-droplets 135 with a volume of approximately 0.2 µL from a unit droplet 130 having a volume of approximately 1 µL.

The example embodiment shown in FIGS. 1(a) and (b) illustrates a device that was fabricated for the demonstration of passive dispensing, attachment of adherent cells, culture and assays of the attached adherent cells, and the detection and measurement of the locally attached adherent cells. As depicted in FIG. 1(a), the bottom plate includes an array of 66 discrete electrodes, including six reservoir electrodes (~34.8 mm² area), six active dispensing electrodes (~6.37 mm² area), and 54 driving electrodes (~4.88 mm² area). The electrode array has inter-electrode gaps of 30-100 µm, and each electrode is connected to an array of contact pads on the side of the device spaced appropriately to interface with a 40-pin connector (not shown).

FIG. 2 illustrates the passive dispensing process, based on a series of droplet dispensing and translation steps. As shown, a virtual microwell containing cells is formed (frames 1-2) followed by two reagent exchanges (frames 3-4 and 5-6). In practice, this process involves 104 droplet movements onto energized electrodes.

Five droplet operations were used in the experiments and example methods described herein. In droplet operation one, reservoir loading, an 8 µL aliquot of reagent was pipetted onto the bottom plate at the edge of the top plate, and loaded by applying driving potential to the appropriate reservoir electrode to draw the fluid into the reservoir.

In droplet operation two, active dispensing, a ~1 µL "unit droplet" was formed on an active dispensing-electrode by pulling and necking from the reservoir. In droplet operation three, active mixing, two 1 µL unit droplets were merged and the combined 2 µL droplet was shuttled back and forth across 10 electrodes 10 times. In droplet operation four, active splitting, a combined 2 µL droplet was split into two unit droplets. In droplet operation five, passive dispensing, a 1 µL unit droplet was actuated across a cell-culture site (on the top plate, above a cell-sensor electrode, as shown in FIG. 1(a)), generating a ~0.2 µL sub-droplet (or "virtual microwell") as described above. The latter process was used both to generate virtual microwells on dry cell-culture sites, and to displace the contents of existing virtual microwells on sites bearing droplets from previous operations.

Four programs were employed when performing example experiments and methods involving the transport, culturing, assaying and detection of adherent cells. The program steps were combinations of the five operations described above.

Program one, cell seeding, was used for fresh devices without cells or virtual microwells, and was implemented in three steps (S1-S3). In step (S1), one or more aliquots of cells suspended in media were loaded into the appropriate reservoirs. In step (S2), one or more unit droplets of cells in suspension were actively dispensed onto the array of electrodes. If more than one unit droplet was to be dispensed from a given reservoir, after each dispensing step, the (old) reservoir volume was removed by wicking with a tissue and replaced with (new) aliquot of cells by repeating (S1). In step (S3), a virtual microwell was generated on a dry cell-culture site from each of the unit droplets generated in (S2), and the remainders of the unit droplets were driven to (a) waste reservoir(s). The remaining contents of all reservoirs were removed with a tissue.

Program two, cell culture, was used for devices with cells in virtual microwells, and was implemented in two steps (C1-C2). In step (C1), the device was flipped upside down (i.e., with the top plate on the bottom) and stored an incubator at 37° C. The inversion of the device ensures that the adherent cells attach to the locally hydrophilic surface regions that reside on the upper plate.

In step (C2), the device was removed from the incubator and returned to its normal orientation (i.e., with top plate on top).

Program three, reagent exchange, was used for devices with cells in virtual microwells, and was implemented in three steps (E1-E3). In step (E1), one or more aliquots of a given reagent were loaded into the appropriate reservoirs. In step (E2), two or more unit droplets of reagent were actively dispensed. If more than four droplets were to be dispensed from a given reservoir, (E1) was repeated after the four dispensing steps to refill the reservoir. In step (E3), the (old) contents of each virtual microwell were replaced with (new) reagent by sequentially passive dispensing two unit droplets onto each cell-culture site. The remainders of the unit droplets were driven to (a) waste reservoir(s), and the contents of all reservoirs were removed with a tissue.

Program four, dilution and exchange, was used for devices with cells in virtual microwells, and was implemented in nine steps (D1-D9). In step (D1), one aliquot each of a reagent and a diluent were loaded into different reservoirs. In step (D2), one 1 µL unit droplet each of reagent and diluent were actively dispensed, then (D3) actively merged and mixed, and then (D4) actively split into two mixed unit droplets. One of the mixed unit droplets was saved for future steps, and in step (D5), the (old) contents of a virtual microwell were replaced with (new) mixed unit droplet onto a cell-culture site. The remainder of the unit droplet was driven to a waste reservoir. In step (D6), a fresh 1 µL unit droplet of diluent was actively dispensed, and then (D7) actively merged and mixed with the saved 1 µL unit droplet (from step D4, above). Steps (D8-D9) were then implemented, which were repeats of (D4-D5). Steps (D6-D9) were then repeated until each cell-culture site had been exchanged with a constituent in the dilution series. At the end of the process, the contents of all reservoirs were removed with a tissue.

Figure 3:
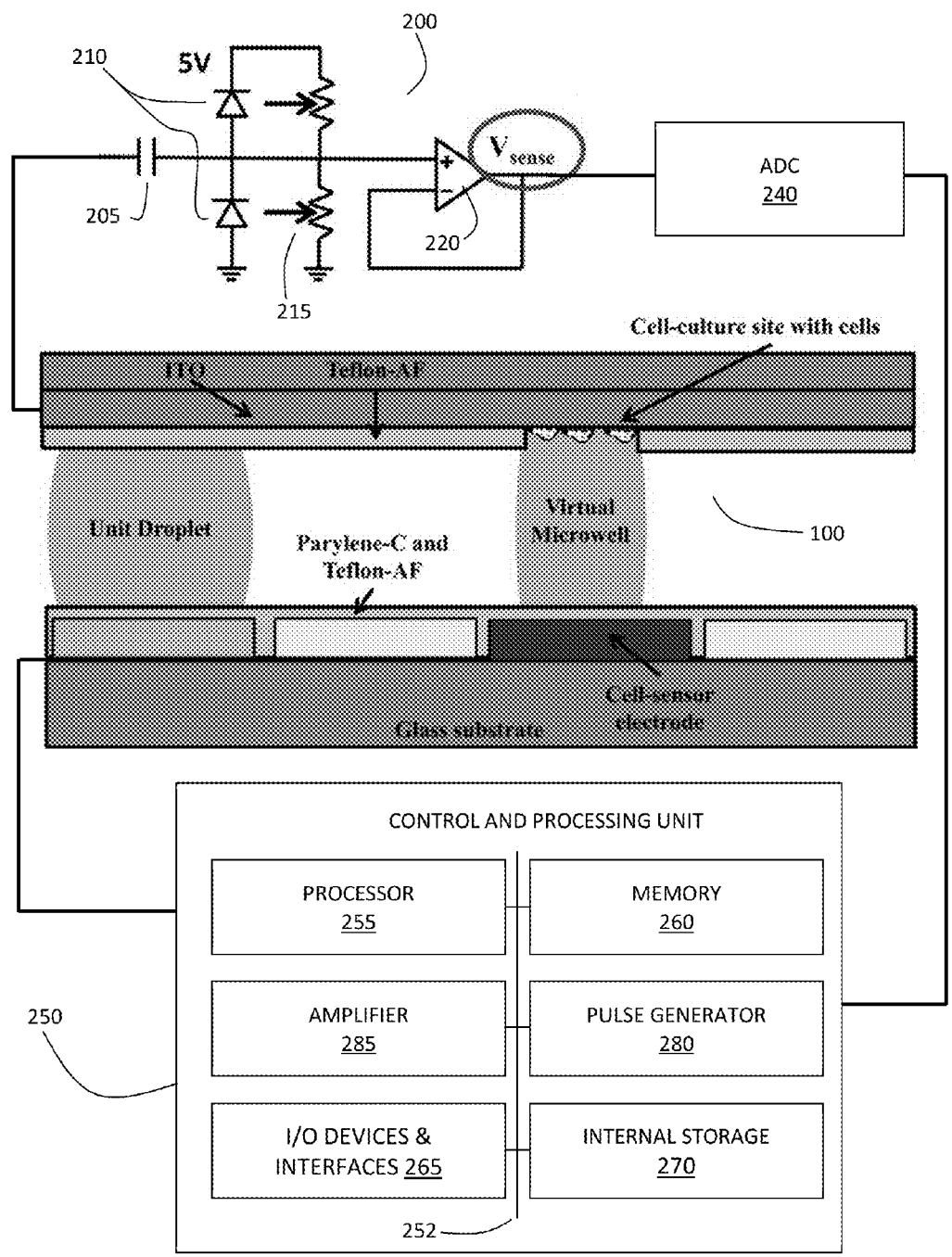
FIG. 3 shows the components of an example system for performing impedance-based measurements of cells on a digital microfluidic platform.

FIG. 3 illustrates an example embodiment of a system for performing impedance measurements and/or detection of adherent cells on a digital microfluidic platform 100. The system generally includes impedance measurement circuit 200, digital microfluidic device 100, analog to digital voltage convertor 240, and control and processing unit 250.

Control and processing unit 250 includes one or more processors 255 (for example, a CPU/microprocessor), a bus 252, memory 260, which may include random access memory (RAM) and/or read only memory (ROM), one or more input/output devices and/or interfaces 265 (e.g. a user input device, such as a keyboard, a keypad, a mouse), one or more internal storage devices 270 (e.g. a hard disk drive, compact disk drive or internal flash memory), and a power supply (not shown). Control and processing unit 250 may include additional components, such as one or more communications interfaces and external storage.

Control and processing unit 250 also includes, or is interfaced to, pulse generator 280 and amplifier 285, which are configured to provide suitable pulses for droplet transport on the digital microfluidic device. For example, pulse generator 280 and amplifier 285 may be configured to deliver 80-120 $V_{RMS}$ droplet driving potentials for selective application to electrodes of digital microfluidic device 100. As described below, the pulses may be provided at a suitable frequency for impedance detection, such as greater than approximately 10 kHz. To move a droplet onto a given destination electrode on the bottom plate, a pulse of driving potential (e.g., with a pulsewidth of approximately 500 ms) is applied to the destination electrode relative to the top-plate electrode.

As shown in FIG. 3, the top plate electrode is connected to capacitor 205 (which may be 1 µF capacitor), voltage clamp 210 (e.g. two 1N4007 diodes), and a digital potentiometer 215 (e.g. model AD5206). According to the present embodiment, the impedance is indirectly measured by measuring $V_{sense}$ at the output of op-amp 220 (e.g. op-amp MCP6004), after applying a suitable voltage across the digital microfluidic device. For example, potentiometer 215 may be triggered or otherwise controlled (for example, by control and processing unit 250) to deliver a suitable percentage (e.g. 5%) of the total applied voltage to the positive terminal of op-amp 250. In one example embodiment, $V_{sense}$ may be measured by applying a suitable pulse length (e.g. a 1 s pulse) with a suitable voltage (e.g. approximately 100 $V_{RMS}$) to the cell-sensor electrode relative to the top-plate electrode at a suitable frequency for sensitivity detection of adherent cells (such as a frequency greater than approximately 10 kHz).

The magnitude of the output voltage, $V_{sense}$, is proportional to the impedance of the volume between the destination electrode on the bottom plate and the top plate electrode. For example, unit droplets of DI water have been measured to have $V_{sense}$=243.6±2.4 mV, and virtual microwells have been measured to exhibit $V_{sense}$=43.6±2.9 mV. The presence of adherent cells at the cell-culture site produces a measurable variation in the impedance of the device, and hence, the value of $V_{sense}$.

Although only one of each component within control and processing unit 250 is illustrated in FIG. 3, more than one of some components can be included in control and processing unit 250. For example, a computer typically contains a number of different data storage media. Furthermore, although bus 252 is depicted as a single connection between all of the components, it will be appreciated that the bus 252 may represent one or more circuits, devices or communication channels which link two or more of the components. For example, in personal computers, bus 252 often includes or is a motherboard.

In one embodiment, control and processing unit 250 includes a general purpose computer or any other hardware equivalents that is programmed to perform the methods disclosed herein. Control and processing unit 250 may also be implemented as one or more physical devices that are coupled to processor 255 through one of more communications channels or interfaces. For example, components of control and processing unit 250 can be implemented using application specific integrated circuits (ASICs). Alternatively, control and processing unit 250 can be implemented as a combination of hardware and software, where the software is loaded into the processor from the memory or over a network connection.

Control and processing unit 250 may be programmed with a set of instructions which when executed in the processor 255 causes the system to perform one or more methods described in the disclosure. Control and processing unit 250 may include many more or less components than those shown.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine-readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

The following section describes experiments that were performed to illustrate the measurement of an electrical signal associated with the impedance of adherent cells on a digital microfluidic platform. In an initial experiment, NIH-3T3 cells at two densities (0.5 and $2\times10^6$ cells/mL) were seeded (S1-S3) and cultured (C1-C2) in virtual microwells for 24 hours. An image of each cell-culture site was captured using a camera mated to a DM2000 upright microscope (Leica Microsystems Canada, Richmond Hill, ON, Canada). ImageJ software (Abramoff et al. 2004) was used to count the number of cells ($N_c$) and calculate the area occupied by the cells ($A_c$), which were $N_c$=60±6.2 cells ($A_c$=2.55×10$^{-2}$ mm$^2$), and $N_c$=177±11.0 cells, $A_c$=1.34×10$^{-1}$ mm$^2$) for the low and high cell densities, respectively.

Figure 4A:
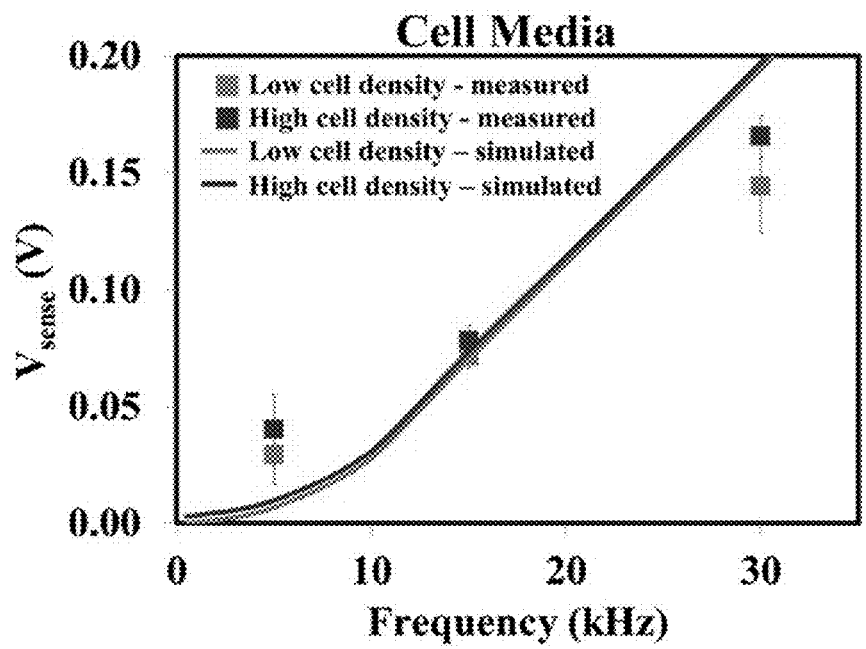
FIGS. 4(a) and 4(b) are graphs showing measured (solid squares; error bars represent ±1 S.D.) and simulated (solid lines) $V_{sense}$ values in (a) cell media and (b) 500 mM sucrose, as a function of frequency. Light and dark grey are indicators for volumetric cell densities of $0.5 \times 10^6$ and $2.0 \times 10^6$ cells/mL, respectively. Simulated $V_{sense}$ values were generated using the circuit model shown in FIG. 6.

$V_{sense}$ values were then measured at three different frequencies, which are shown in FIG. 4(a) as discrete points for the low and high density cases. The differences between these values were not statistically significant. For example, at 15 kHz, the $V_{sense}$ values were 71.5±4.9 mV and 78.3±6.6 mV respectively (p=0.101). This suggests that these conditions were not ideal for measuring cell density as a function of impedance.

In order to improve the correlation between $V_{sense}$ and cell density, and the overall sensitivity of the system, a buffered, iso-osmotic medium with lower conductivity than cell media, was delivered in a media exchange step prior to the measurement of $V_{sense}$. In an example implementation, the media in virtual microwells was exchanged with a low-conductivity sucrose solution (as in FIG. 2, frames 3-4) prior to measuring $V_{sense}$.

Accordingly, in a second experiment, after step C2, the culture media was exchanged (E1-E3) with aqueous sucrose (500 mM in DI water with 10 mM HEPES, 0.05% w/v Pluronic F68, pH 7.4) immediately prior to measurement of $V_{sense}$ using the same parameters as above. Each condition was replicated five times, and paired t-tests were used to evaluate statistical significance.

Figure 4B:
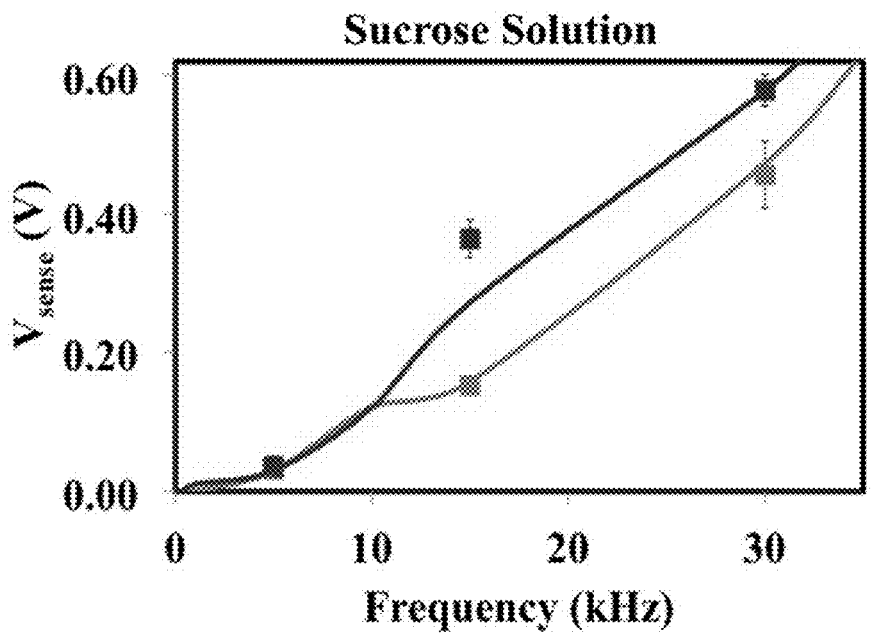

These data are shown as discrete points in FIG. 4(b), and reveal that sensitive detection may be achieved beyond a suitable detection frequency. For example, for measurements at 15 kHz, the $V_{sense}$ values for low and high densities were 151.2±11.9 mV and 364.6±27.4 mV. This difference is significant (p=2.36×10$^{-7}$), and confirms that low-conductivity liquids are favourable for impedance sensing of cells. Methods were developed to rapidly exchange the sucrose solution with fresh cell culture media (as in FIG. 2, frames 5-6) after the analysis. In typical experiments, this resulted in cells being exposed to the sucrose solution for ~10 min, a condition which did not impact cell proliferation rates for any of the cell types evaluated here.

Accordingly, in some embodiments, a passive dispensing step may be performed to replace a droplet of cell culture medium with a droplet of a low-conductivity medium. The low-conductivity medium has a conductivity (or ionic strength) that is lower than that of the cell culture medium.

In some embodiments, the low-conductivity medium exhibits approximately the same osmolarity as the cell culture medium, or as a typical cell culture medium. In other embodiments, the low-conductivity medium is approximately iso-osmotic relative to the adherent cells that are attached to the hydrophilic surface. Non-limiting examples of suitable low-conductivity, cell-compatible additives include sucrose, mannitol, dextrose, sorbitol, and/or other inert fillers.

In other embodiments, the low-conductivity medium has a composition that is compatible with the adherent cells, such that the adherent cells remain viable after exposure or contact with the low-conductivity medium. The exposure time may vary depending on the application of the method. In some implementations, the adherent cells may only be exposed to the low-conductivity medium for a short time duration, such as a time duration on the order of seconds. In such cases, the conditions placed on the composition of the low-conductivity medium to support cell viability or compatibility may be more relaxed. For example, the composition of the low-conductivity medium may be selected such that the exposure of the adherent cells to the low-conductivity medium would be toxic to the adherent cells over longer timescales, but non-toxic over short exposure durations.

Figure 5:
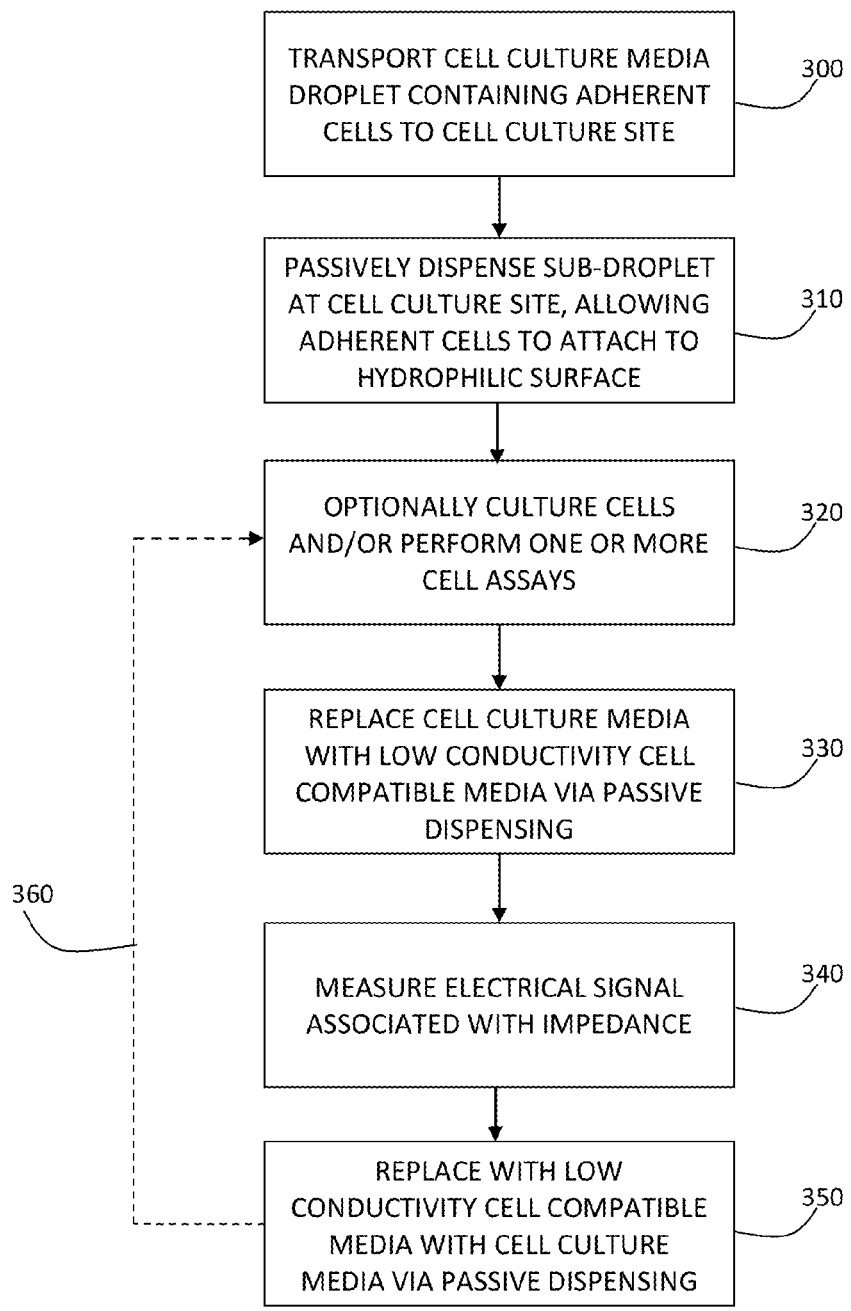
FIG. 5 is a flow chart illustrating an example method of performing impedance measurements of adherent cells using a digital microfluidic platform.

Referring now to FIG. 5, a flow chart is provided that illustrates an example method in which an electrical signal associated with impedance is employed for the measurement and/or detection of adherent cells on a digital microfluidic platform. In step 300, a droplet of cell culture media, containing adherent cells, is transported, via activation of the discrete electrodes on a digital microfluidic array, to a cell-culture site (i.e. a locally hydrophilic surface region). Passive dispensing is employed in step 310 to dispense a sub-droplet containing adherent cells at the cell-culture site. The adherent cells in the sub-droplet subsequently attach to the hydrophilic surface at the cell-culture site. If the cell-culture site is provided on the top plate of the digital microfluidic device, then the device may be inverted during this process.

As shown at step 320, the adherent cells may be cultured at the cell-culture site, and/or one or more cell assays may be performed, where the detection step may be performed in a subsequent impedance measurement step, as described below. This step may include one or more passive dispensing steps for replenishing cell culture media. Furthermore, in any cases in which the adherent cells are attached to the top plate of the digital microfluidic device, incubation steps may be performed with the device inverted.

In step 330, a passive dispensing step is performed to replace the cell culture media sub-droplet with a low-conductivity, cell-compatible liquid or buffer droplet, suitable for the subsequent impedance measurement step. As noted above, an example liquid is a sucrose solution with a concentration of approximately 500 mM. After performing the passive dispensing media exchange step, the impedance, or an electrical signal associated with the impedance, is measured and recorded, as shown in step 340. As described above, the impedance, or an electrical signal associated with the impedance, may be measured above a threshold frequency, such that suitability signal to noise (or limit of detection) is obtained.

In step 350, a subsequent passive dispensing step may be employed to replace the low-conductivity, cell-compatible liquid droplet with a droplet of cell culture media, should it be desirable to preserve the viability of the cells. After an optional cell culture or cell assay step, the media exchange and impedance detection process may be repeated one or more times, as shown at step 360.

Although the example embodiments described herein involve the measurement of a voltage that is associated (for example, proportional) to impedance, it is to be understood that the impedance, or any electrical signal associated with impedance (directly or indirectly), may be measured in order to electrically measure, detect, enumerate, or otherwise characterize the attached adherent cells. For example, other circuits that may be employed to sense an electrical signal associated with the impedance of the adherent cells include a voltage divider, a bridge electrical circuit, and a sensor electrode and a counter electrode connected to a lock-in amplifier. In the latter case, the counter electrode may be larger than the sensor electrode.

In some embodiments, the signal associated with impedance may be employed to detect the presence of one or more adherent cells, and/or to measure one or more properties or measures associated with the adherent cells. For example, as described in the examples provided herein, the electrical signal associated with impedance may be employed to provide a measure associated with the quantity, density, and/or surface area coverage of the attached adherent cells.

Figure 6:
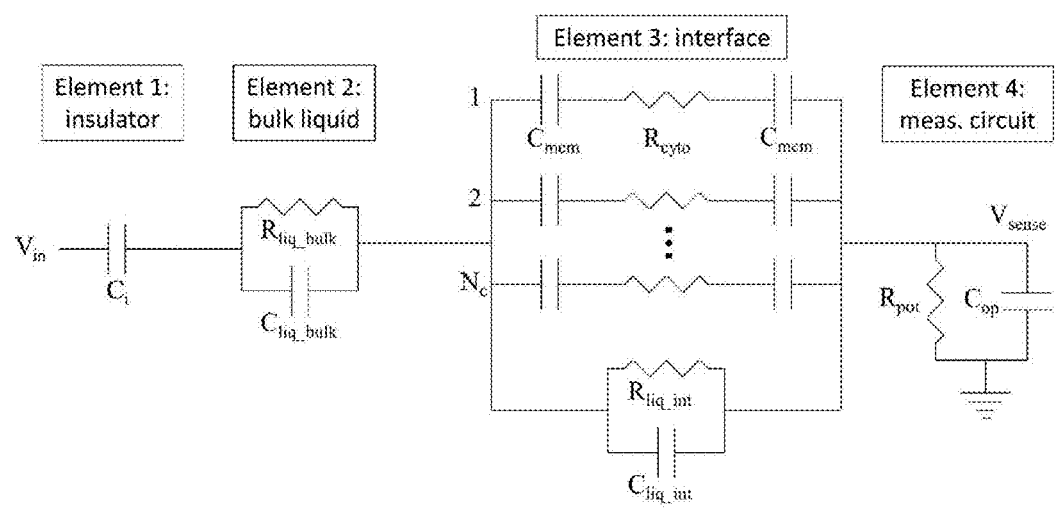
FIG. 6 shows a model circuit used in LTSPICE simulations.

To investigate the experimental results described above, a circuit model was developed, as shown in FIG. 6. Circuit 400 was adapted from those described previously (Morgan et al. 2007; Sun and Morgan 2010; Sun et al. 2010), and includes a resistor 410 and a capacitor 415 in parallel to model the liquid medium (element 2 in FIG. 6) and capacitors and a resistor in series to model the cell membrane and cytoplasm respectively (the top sub-circuit of element 3 in FIG. 6).

The models used previously are suitable to model the conditions of the present embodiments. One key difference is the presence of the insulator covering the bottom-plate electrode of the digital microfluidic device. In order to account for this difference, a capacitor (element 1 in FIG. 6) was added to the model.

A second difference is in embodiments in which adherent cells are employed, the cells are adhered to one of the electrodes, whereas the models used previously were designed for a system in which cells were not in contact with the electrodes. To accommodate this difference, a separate sub-circuit was included to model liquid at the interface between the droplet and the electrode (the bottom sub-circuit of element 3 in FIG. 6).

As shown in the Figure, the circuit has four elements in series. The first element represents the parylene insulator on the bottom-plate of the device, modeled as a capacitor ($C_i$). The second element represents the bulk droplet, modeled as a resistor and a capacitor ($R_{liq\_bulk}$ and $C_{liq\_bulk}$) in parallel. The third element represents the interface between the droplet and the top-plate electrode (arbitrarily chosen to be 10 μm thick), and contains two sub-circuits (in parallel). The first sub-circuit represents the cells at the interface, with each cell modeled as two capacitors and a resistor ($C_{mem}$, $R_{cyto}$, $C_{mem}$) for $N_c$ cells in parallel. The second sub-circuit represents the liquid at the interface, modeled as a resistor and a capacitor ($R_{liq\_int}$ and $C_{liq\_int}$) in parallel. The fourth circuit element represents the potentiometer and the internal capacitance of the op-amp ($R_{pot}$ and $C_{op}$) in the measurement circuit. The circuit model does not include representations of cell membrane resistance or cytoplasm capacitance, the coupling capacitor (1 μF), or the resistance or capacitance of the thin layers of Teflon®-AF, which are assumed to have negligible effects.

The electrical properties of each element in the circuit model are listed in FIG. 7. Values that were not known, measured, or found in the literature were calculated according to equations 1 and 2, $$R = \frac{\rho l}{A} \qquad \text{Eq. 1}$$

$$C = \frac{\varepsilon_0 \varepsilon_r A}{t} \qquad \text{Eq. 2}$$

where t, A, ρ and $\varepsilon_r$ are the thickness, area, resistivity, and dielectric constant of the material, and $\varepsilon_o$ is the permittivity of free space. $V_{sense}$ as a function of frequency (0-35 kHz) was simulated using LTSpice (Linear Technology, Milipitas, Calif.) with a 100 $V_{RMS}$ sinusoidal source.

The simulated data for four conditions (cell media/high cell density, cell media/low cell density, sucrose/high cell density, sucrose/low cell density) were compared with experimental measurements (described above). $V_{sense}$ values predicted by the circuit model are plotted as solid lines in FIG. 4. The key experimentally observed trends are reproduced by the simulated curves, including accurate predictions that lower conductivity media and higher analysis frequencies are preferable for correlating impedance to cell density.

Accordingly, in one embodiment, when preforming impedance detection, the electrical measurements are preformed above a threshold frequency, in order to obtain suitable signal-to-noise (i.e. sensitivity or limit of detection). Although the examples provided herein suggest a threshold frequency in the range of approximately 10 kHz, it is to be understood that a suitable threshold frequency may differ among different adherent cell types, circuit parameters of the digital microfluidic device, and other properties of the digital microfluidic device, such as geometrical properties. Accordingly, those skilled in the art may perform a frequency investigation for a given device and/or cell type in order to determine a suitable threshold frequency.

It is noted that there are a number of potential causes for the differences between the experimental and simulated data. One potential source of variation is changes in the effective area of the electrode observed as a function of changes in droplet contact angle. A second potential source of variation is imperfect estimation of area occupied by the cells in the model, and a third is imperfect estimation of cell membrane capacitance and cytoplasm resistance. Those skilled in the art may refine the model parameters without departing from the scope of the present disclosure, in order to obtain better concordance between the measured and simulated results.

The model also suggests that the sensitivity to variations in cell density, or equivalently the limit of detection, can be controlled by varying a number of parameters of the device, including the thickness of the dielectric, insulating layer covering one of the electrodes, the spacing between top and bottom plate, and the electrode area. Indeed, simulations show that reducing any or all of these parameters can produce an increase in sensitivity.

Figure 8:
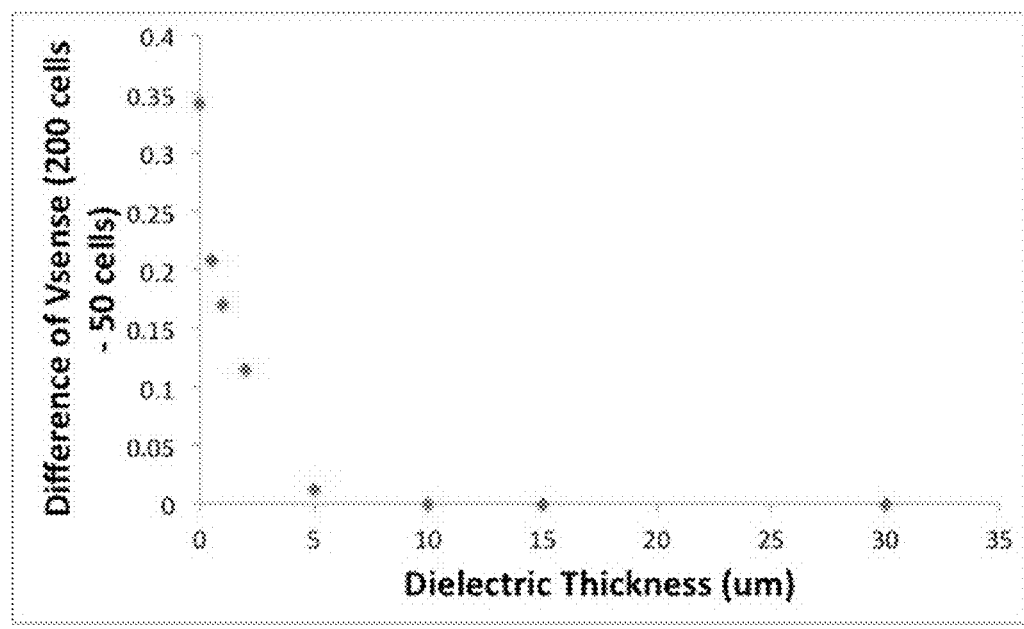
FIG. 8 plots the dependence of the sensitivity of cell detection on the thickness of the dielectric layer covering one of the sensing electrodes.

In one example, simulations were employed, using the aforementioned circuit model, to evaluate the effects of insulator thickness on impedance measurement sensitivity. FIG. 8 plots the difference between $V_{sense}$ (the signal measured by the system that correlates with impedance) predicted by the circuit model for 200 cells and 50 cells as a function of insulator thickness. A larger value for this difference indicates greater sensitivity (i.e., improved ability to distinguish between different densities of cells and lower overall detection limits). Accordingly, as insulator thickness is reduced, the sensitivity of the measurement is increased. Embodiments described in further detail below employ this principle, including dedicated sensing electrodes (in addition to electrodes for droplet translation) that are used for cell sensing. These dedicated sensing electrodes could be covered with a thinner insulator (or bare electrodes with no insulator), which would allow for improved impedance sensing performance.

Accordingly, in one example embodiment, the thickness of the dielectric layer covering one of the sensing electrodes may be between approximately 0 and 15 microns. A device with improved sensitivity may be obtained by selecting the dielectric thickness to be between approximately 0 and 5 microns. It is to be understood that this dielectric thickness may be a global dielectric thickness that is common across all or a substantial portion of the device, or this dielectric thickness may be configured locally, for example, in the vicinity of the sensing electrode. The latter could be formed by reactive ion etching to locally remove the dielectric layer, or a portion thereof. In embodiments including a virtual microwell formed by providing a local hydrophilic area, the dielectric thickness may be configured locally for one or more electrode in the vicinity of the virtual microwell. Finally, in selected embodiments, the dielectric thickness may be selected to be zero, such that both electrodes are bare.

Furthermore, in one example embodiment, the electrode area for the sensing electrode may be between approximately 500 and $10^7$ $\mu m^2$. It is to be understood that this electrode area may be a global electrode area that is common across all or a substantial portion of the device, or this electrode area may be configured locally, for example, for only the sensing electrode. In embodiments including a virtual microwell formed by providing a local hydrophilic area, the electrode area may be configured locally for one or more electrodes in the vicinity of the virtual microwell.

Furthermore, in one example embodiment, the spacing between the top and bottom plate may be between approximately a few nm and 100 μm. It is to be understood that this spacing may be a global spacing that is common across all or a substantial portion of the device, or this spacing may be configured locally, for example, in the vicinity of the sensing electrode. In embodiments including a virtual microwell formed by providing a local hydrophilic area, the spacing may be configured locally in the vicinity of the virtual microwell.

It is further noted that in cases where the sensitivity of the impedance measurement is increased due to any of the modifications discussed above, then it may be possible to perform impedance measurements directly, without replacing the cell culture medium with the low-conductivity medium. The increased sensitivity may also support the detection of impedance-based signals when the adherent cells are exposed to other liquid compositions, such as reagents employed when performing cell assays.

It is to be understood that variations of this method may be useful for a wide range of assays. For example, assay in which cell proliferation rate is employed as the readout—e.g., drug screening (Kunas and Papoutsakis 2009; Mengual Gomez et al. 2010; Otto et al. 2003; Stolwijk et al. 2011), gene expression (Zudaire et al. 2008), and wound healing (Keese et al. 2004; Lundien et al. 2002) may be performed in a digital microfluidic, impedance-based method, according to embodiments disclosed above.

Furthermore, it is to be understood that device and methods according to the present disclosure may be configured to support multiplexed processing of cell-containing droplets and multiple hydrophilic cell-culture sites for the multiplexed detection of electrical impedance signals.

Although the cell-culture sites described in the examples provided herein related to hydrophilic regions produced by complete removal of a dielectric layer covering an electrode, it is to be understood that a local hydrophilic region suitable for passive dispensing, culture, and/or local impedance detection may be formed according to a variety of methods. Non-limiting examples of forming locally hydrophilic sites include depositing (microprinting, microstamping) a biosubstrate (such as extracellular matrix proteins), rendering a hydrophilic and charged surface via microfabrication, and other cell-specific surface modification procedures. A hydrophilic bio-substrate can be also formed by dispensing a droplet of a bio-substrate solution in a DMF device and translating it to the desired location of the cell-culture site, where after incubation and drying, it forms a bio-substrate layer for cell attachment. Other methods for producing the hydrophilic areas include, but are not limited, to microfabrication techniques (e.g. exposing hydrophilic layers of a device, such as glass or electrodes, in specific areas), surface plasma treatment, or deposition of a thin, patterned, hydrophilic layer onto a device surface.

In some embodiments, a digital microfluidic device for measuring cell impedance may include two sensing electrodes on opposing plates of a two-plate digital microfluidic device, where a surface above one or both sensing electrodes is hydrophilic, and wherein one electrode, both electrodes, or neither electrode is covered with a dielectric layer.

In some embodiments, an outer surface associated with only one of the two electrodes is hydrophilic, such that cells attach on only one of the two plates of the device.

In some embodiments, a dielectric layer may cover both electrodes, where a top surface of the dielectric layer associated with at least one electrode is hydrophilic. In such embodiments where both electrodes are covered with a dielectric layer, the thickness of the dielectric layer above each electrode may be selected to be sufficiently thin to support the detection of suitable quantity and/or density of attached adherent cells.

In the aforementioned embodiments, the pre-selected electrodes on the bottom plate are employed both for droplet translation and for impedance sensing, as can be seen in the example embodiment shown in FIG. 1(a). However, it is to be understood the one or more of the sensing electrodes need not also be employed for droplet translation, and may alternatively be dedicated sensing electrodes. As further described below, in embodiments in which the sensing electrode is a dedicated electrode, a greater degree of design flexibility is obtained. For example, in such cases, the sensing electrode need not include a dielectric layer, or may be located locally on top of a dielectric layer.

Figure 9A:
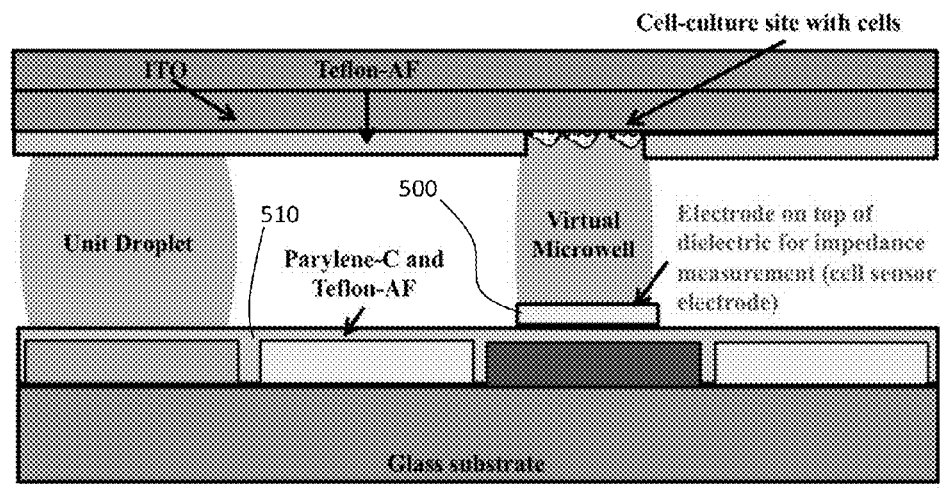
FIGS. 9(a) to 9(d) illustrate an alternative embodiment in which a dedicated sensing electrode is formed on top of the dielectric layer of the bottom plate.

One such alternative embodiment is illustrated in FIG. 9(a), which shows a side view of a device that is a variation of the embodiment show in FIG. 1(b). As shown in the Figure, sensing electrode 500 is a bare electrode that is located on top of dielectric layer 510. This bare electrode configuration may provide superior performance, as suggested by the simulation results shown in FIG. 8.

Figure 9B:
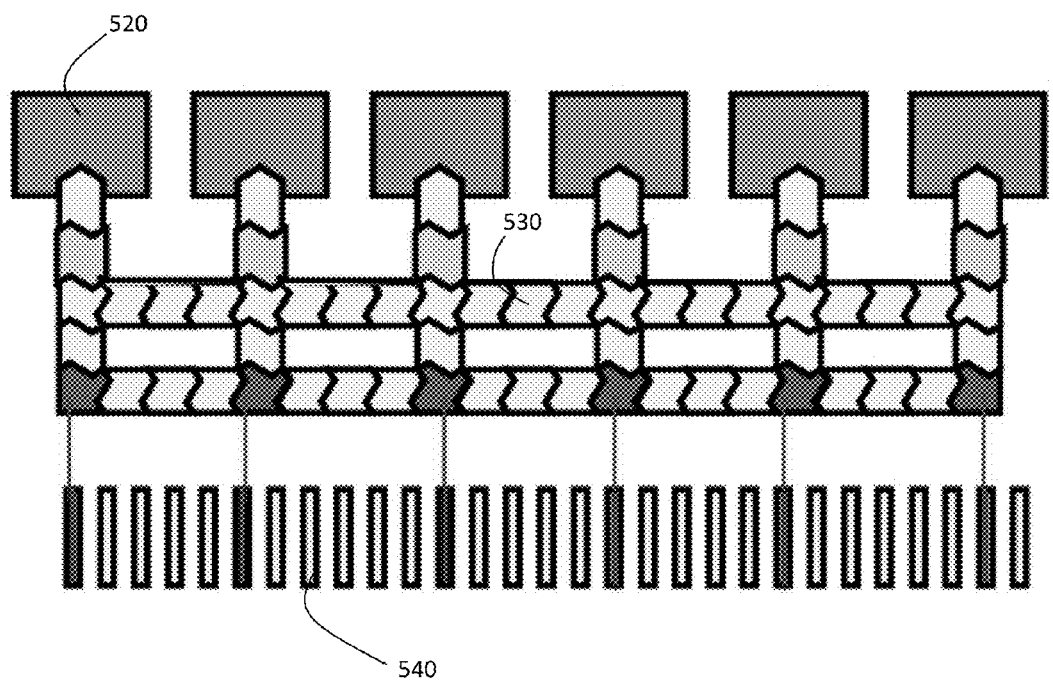
Figure 9C:
Figure 9D:
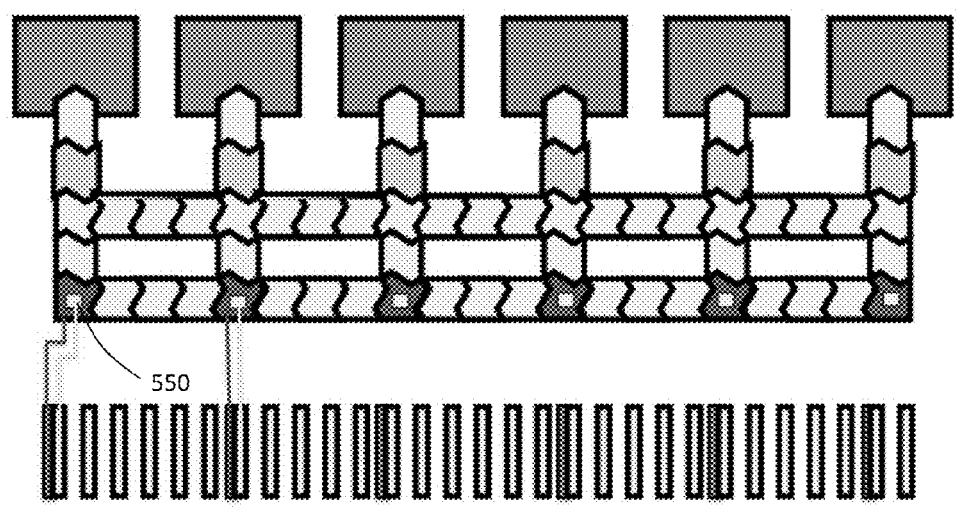

FIGS. 9(b) through 9(c) illustrate the example masks for photolithographically forming electrodes to produce the device shown in FIG. 9(a). The mask shown in FIG. 9(b) includes features for forming reservoir electrodes 520, array electrodes 530, and contact pad electrodes 540. After forming these electrodes in a first electrode layer, dielectric layer 510 is formed. A subsequent photolithography step is then performed using the mask shown in FIG. 9(c), which includes features for forming dedicated sensing electrodes 550 and contact pads 560. The composite structure is illustrated in plan view in FIG. 9(d), where dedicated sensing electrodes 550 are formed on the dielectric layer, above the array electrodes.

Figure 10:
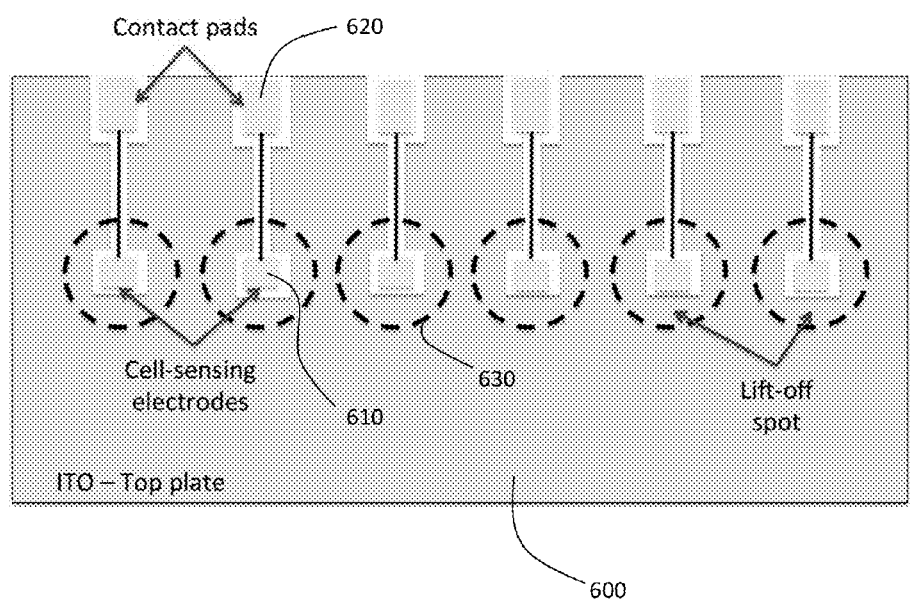
FIG. 10 illustrates an embodiment in which dedicated sensing electrodes are formed within the ITO layer of the top plate.

FIG. 10 illustrates another alternative embodiment, in which dedicated sensing electrodes 610 that are connected to contact pads 620 are defined within the ITO layer 600, such that the dedicated sensing electrodes 600 may be independently addressed relative to the common ITO electrode. As shown in the Figure, a lift-off process may be employed to create cell-culture sites 630 that expose the dedicated cell sensing electrodes 600.

Figure 11A:
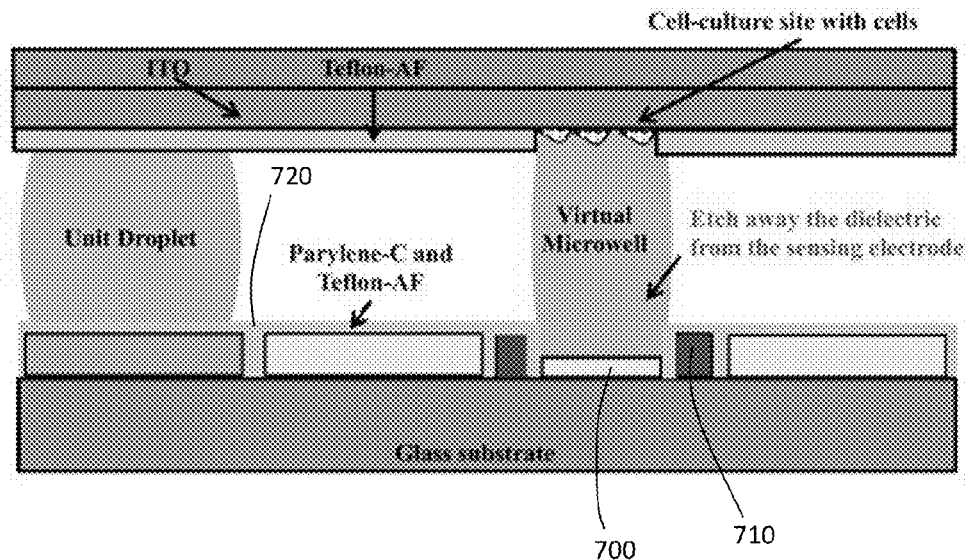
FIGS. 11(a) and 11(b) illustrate an alternative embodiment in which a dedicated, and locally exposed, sensing electrode is formed within a central region of an array electrode.
Figure 11B:
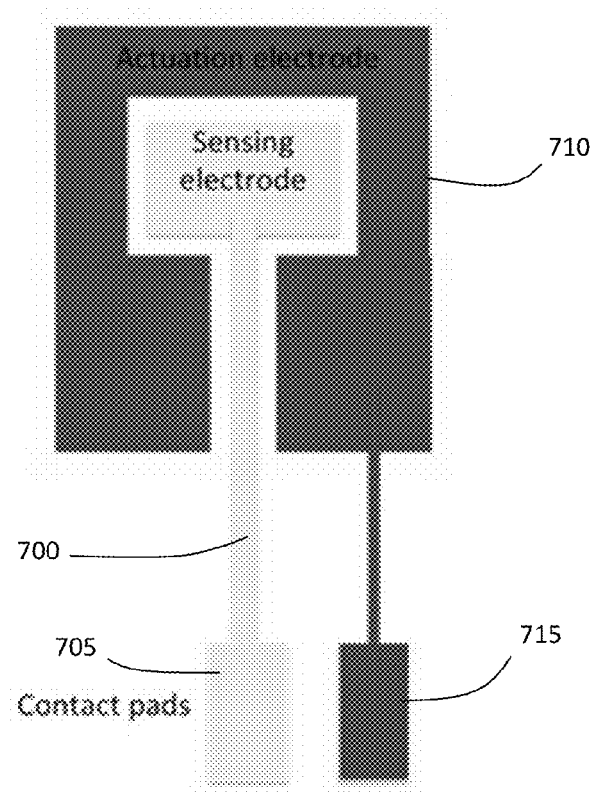

In FIGS. 11(a) and 11(b), another alternative embodiment is illustrated in which a dedicated, and independently addressable sensing electrode 700, is formed in a region within array electrode 710. As shown in FIG. 11(b), sensing electrode 700 may be photolithographically defined such that it is electrically isolated from array electrode 710, and formed within a central region of array electrode 710, and where dielectric layer 720 is locally removed such that only sensing electrode 700 is exposed. As shown in the Figure, at least a portion of sensing electrode 700 is surrounded by at least a portion of the array electrode 710. Reactive ion etching may be employed to locally remove the dielectric layer and expose the sensing electrode 700. Sensing electrode 700 and array electrode 710 may be addressed by contact pads 705 and 715, respectively.

It is noted that in embodiments such as those shown in FIG. 9(a) and FIG. 11(a), where bare electrodes are exposed on both the top plate and the bottom plate and where both electrodes have a hydrophilic surface, adherent cells may attach (and grow) on either surface. In practice, however, the adherent cells would typically only grow on one plate surface, due to gravity. As such, in some embodiments, a given electrode onto which adherent cells are to be attached may be selected by orienting the digital microfluidic device such that the plate having the selected electrode is the on the bottom. This step may be only need to be performed during initial incubation of an adherent cell containing droplet with the hydrophilic surface, i.e. during the initial attachment step.

As described above; embodiments of the present disclosure provide a platform that is suitable for the sensing of the impedance of cell-containing droplets, and in particular, in droplets containing adherent cells. The digital microfluidic impedance systems disclosed herein support label-free detection and do not require imaging, and are compatible with long-term cell culture.

The present embodiments may enable a substantial reduction (e.g. 1000-fold) in reagent use compared to commercially available cell impedance analysis systems. For example, the Applied Biophysics ECIS® system requires 1.5-4 mL per assay (Giaever and Keese 1991; Tiruppathi et al. 1992), while corresponding assay requires 1-10 µL in a digital microfluidic format according to the embodiments disclosed herein.

Furthermore, as discussed above, the digital microfluidic impedance sensing format and method, as presently disclosed, uniquely enables controlled and repeated media exchange, and exchange of suitable buffers for sensitive impedance measurement, without external intervention, thereby supporting culture and analysis for potentially long periods of time. The methods described herein may be particularly useful for applications involving small numbers of precious cells and for assays involving frequent media/reagent exchange steps. In particular, the embodiments disclosed herein may be employed to perform multiplexed cell culture and cell assays, with sensing based on impedance, in a format that is convenient for high-throughput screening applications. In some applications, the present embodiments may obviate the need for optical testing, thereby significantly simplifying the complexity of the instrumentation needed for ongoing monitoring of cells assays in high throughput screening applications.

The following examples are presented to enable those skilled in the art to understand and to practice embodiments of the present disclosure. They should not be considered as a limitation on the scope of the present embodiments, but merely as being illustrative and representative thereof.

EXAMPLES

Example 1

Digital Microfluidic Device Fabrication

Digital microfluidic device bottom-plates bearing patterned electrodes and contact pads were formed by photolithography and etching. Briefly, gold- and chromium-coated substrates were spin-coated with S1811 photoresist (3000 rpm, 30 s). The substrates were pre-baked on a hot-plate (100° C., 2 min) and exposed to UV through a photomask for 10 s (30 mW cm$^{-2}$) and then developed by immersing in MF-321 for ~3 min. Gold was etched by immersing in gold etchant (~5 min), followed by chromium etching by immersing in CR-4 (~10 s). Substrates were then immersed in AZ 300T (5 min) to remove the photoresist and finally washed in DI water and dried under a stream of nitrogen. These devices were then coated with 2 μm of Parylene-C and 50 nm of Teflon®-AF. Parylene-C was applied using a vapor deposition instrument (Specialty Coating Systems), and Teflon®-AF was spin-coated (1% wt/wt in Fluorinert FC-40, 1000 rpm, 30 s) followed by post-baking on a hot-plate (160° C., 10 min). Dicing tape was placed on the electrode contact pads prior to parylene coating and was removed after Teflon®-AF coating to facilitate electrical contact.

Digital microfluidic device top-plates were formed from ITO-glass substrates coated with 50 nm Teflon®-AF using the same procedure described for bottom plates (as above). The Teflon®-AF was patterned by lift-off to feature six 1 mm diameter circular regions of exposed ITO (known as "cell-culture sites") spaced 9 mm apart using methods described previously (Eydelnant et al. 2012). As shown in FIGS. 1(a) and 1(b), devices were assembled with an ITO-glass top plate and a gold-on-glass bottom plate separated by a spacer formed from 2 pieces of double-sided tape (total thickness of 180 μm), such that each cell-culture site on the top plate was aligned over a cell-sensor electrode. Moreover, each 25 mm×75 mm top plate was roughly aligned with the outer-edges of the reservoir electrodes on the bottom plate.

Example 2

Digital Microfluidic Cell Impedance Assays

An example digital microfluidic impedance measurement system was validated in three assays: calibration, proliferation, and serum sensing. In the first assay, three cell lines (HeLa, CHO-K1, and NIH-3T3) were seeded at different densities to determine the relationship between impedance and cell number, which was found to be linear for each type of cell. In the proliferation assay, cells were grown for four days and their proliferation rates were determined by regular impedance measurements. In the serum sensing assay, a dilution series of cell media containing different concentrations of serum was evaluated using impedance measurements to determine the optimum conditions for proliferation In calibration assays, suspensions of HeLa, NIH-3T3, and CHO-K1 cells at different volumetric densities (0.5, 1, and 2×10$^6$ cells/mL) were seeded (S1-S3), cultured (C1-C2) for 24 h, the solution was exchanged with aqueous sucrose (E1-E3), and V$_{sense}$ was measured at 15 kHz. Each condition was replicated five times and image-based cell surface densities and areas occupied by cells were calculated as above. Lines of regression were generated to relate V$_{sense}$ to cell surface density.

Figure 12:
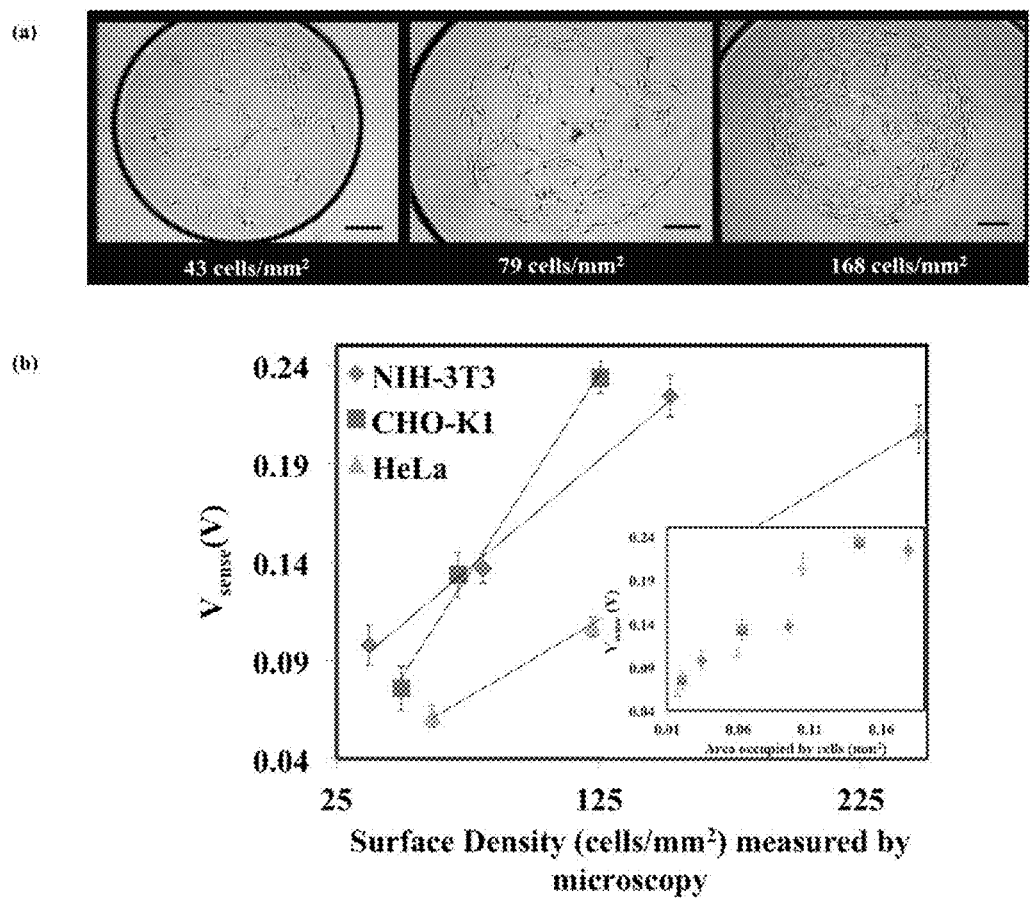
FIGS. 12(a) and 12(b) show the results from calibration assays.

Images were used to calculate the resulting surface densities and areas occupied by the cells (FIG. 12(a)), and V$_{sense}$ was then plotted as a function of cell surface density (FIG. 12(b)). The regression lines were linear (R$^2$=0.9920, 0.9935, 0.9965 for CHO-K1, NIH-3T3, and HeLa cells) over at least one order of magnitude (higher densities were not tested). The limits of detection (LOD) were ~20-25 cells/mm$^2$. The apparent differences between cell lines can be partly explained by differences in cell area (FIG. 12(b)—inset); any remaining differences are likely a function of the known differences in capacitive coupling for different cell types (Giaever and Keese 1991; Holmes et al. 2009).

In proliferation assays, suspensions of HeLa, NIH-3T3, and CHO-K1 cells at a volumetric density of 0.25×10$^6$ cells/mL were seeded (S1-S3), cultured (C1-C2) for 24 h, and exchanged with aqueous sucrose (E1-E3). V$_{sense}$ at 15 kHz was measured and translated to a cell surface density using regression curves generated in the calibration assay. The sucrose solution was then exchanged with cell media (E1-E3) and then the cells were cultured (C1-C2) for 24 h. This process (E1-E3 with aqueous sucrose, measurement of V$_{sense}$, E1-E3 with fresh media, and C1-C2 for 24 h) was repeated after 48, 72, and 96 h. Each condition was replicated five times.

FIG. 13(a) shows growth curves for each cell line, in which V$_{sense}$ values were translated to surface cell densities from the data in FIG. 12(b). As shown, on day 1, cell numbers were below the detection limits, but on each later day measurable values were obtained. The trend of NIH-3T3 and HeLa cells proliferating faster than CHO-K1 cells (highlighted in FIG. 13(b)) was identical to that observed for cells cultured in standard conditions.

In serum screening assays (motivated by the wide-spread interest in reducing the serum content in in vitro cell culture (Ikeda et al. 1995; Mengual Gomez et al. 2010)), NIH-3T3 cells were seeded and grown in a dilution series of fetal calf serum at different concentrations (generated on-chip) for four days, with periodic impedance measurements to evaluate cell density (FIG. 13(a)).

NIH-3T3 cells in complete media at a volumetric density of 0.25×10$^5$ cells/mL were seeded (S1-S3) and cultured (C1-C2) for 6 h. A dilution and exchange program was then executed to generate droplets containing five different concentrations of FCS (fetal calf serum) (0.63%, 1.25%, 2.5%, 5%, and 10%) in media using DMEM fortified with 100 IU/mL penicillin, 100 μg/mL streptomycin, 0.05% w/v Pluronic F-68, and 20% FCS as "reagent", and the same solution without FCS as "diluent" for steps (D1-D9). Cells in virtual microwells containing each of these serum concentrations were then cultured (C1-C2) for 24 h and then exchanged with aqueous sucrose (E1-E3). V$_{sense}$ at 15 kHz was measured and this value was translated to a cell surface density using the regression curve from the calibration assay.

Media containing different concentrations of serum were then re-generated and used to exchange the sucrose solutions in the virtual microwells (D1-D9) and the cells were cultured (C1-C2) for an additional 24 h. This process (E1-E3 with aqueous sucrose, measurement of V$_{sense}$, D1-D9 to generate and replace with fresh media with different FCS concentrations, and C1-C2 for 24 h) was repeated after 48 and 72 h, culminating with a final analysis (E1-E3 with aqueous sucrose and measurement of V$_{sense}$) after 96 h. Each condition was replicated five times.

As shown in FIG. 14(a), at 5% and 10% serum, cell growth followed sigmoidal profiles, while at lower concentrations cells did not grow well. As depicted in FIG. 14(b), the method was carried out in 6-plex format, and it would be straightforward to expand this technique to higher levels of multiplexing, particularly with the recent report of digital microfluidic devices with 4096 independent electrodes (Hadwen et al. 2012).

Example 3

Macro-Scale Cell Culture

HeLa, NIH-3T3, and CHO-K1 cells were grown in complete cell culture media formed from DMEM (HeLa and NIH-3T3) or 50/50 v/v F-12/DMEM (CHO-K1), supplemented with 10% fetal calf serum (FCS), penicillin (100 IU/mL) and streptomycin (100 µg/mL). Cells were grown to near confluency in complete media in T-25 flasks in an incubator at 37° C. with 5% $CO_2$. Prior to each digital microfluidic experiment, cells were detached using a solution of trypsin (0.25% w/v) and EDTA (1 mM), centrifuged, then resuspended in complete media supplemented with 0.05% Pluronic F68 (w/v) at the appropriate density.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

Abdelgawad, M., Wheeler, A. R., 2009. Adv Mater 21, 920-925
Abdolahad, M., Taghinejad, M., Taghinejad, H., Janmaleki, M., Mohajerzadeh, S., 2012. Lab on a Chip 12, 1183-1190
Abramoff, M. D., Magalhaes, P. J., Ram, S. J., 2004. Biophotonics International 11, 36-42
Adams, A. A., Okagbare, P. I., Feng, J., Hupert, M. L., Patterson, D., Gottert, J., McCarley, R. L., Nikitopoulos, D., Murphy, M. C., Soper, S. A., 2008. Journal of the American Chemical Society 130, 8633-8641
Asphahani, F., Thein, M., Veiseh, O., Edmondson, D., Kosai, R., Veiseh, M., Xu, J., Zhang, M., 2008. Biosens Bioelectron 23, 1307-1313
Ayliffe, H. E., Frazier, A. B., 1999. Journal of Microelectromechanical Systems 8, 50-57
Barbulovic-Nad, I., Au, S. H., Wheeler, A. R., 2010. Lab on a Chip 10, 1536-1542
Barbulovic-Nad, I., Yang, H., Park, P. S., Wheeler, A. R., 2008. Lab on a Chip 8, 519-526
Boeck, G., 2001. International Review of Cytology—a Survey of Cell Biology 204, 239-298
Bogojevic, D., Chamberlain, M. D., Barbulovic-Nad, I., Wheeler, A. R., 2012. Lab on a Chip 12, 627-634
Brischwein, M., Herrmann, S., Vonau, W., Berthold, F., Grothe, H., Motrescu, E. R., Wolf, B., 2006. Lab on a Chip 6, 819-822
Chen, J., Zheng, Y., Tan, Q., Zhang, Y. L., Li, J., Geddie, W. R., Jewett, M. A., Sun, Y., 2011. Biomicrofluidics 5, 14113
Cheng, X., Liu, Y. S., Irimia, D., Demirci, U., Yang, L., Zamir, L., Rodriguez, W. R., Toner, M., Bashir, R., 2007. Lab on a Chip 7, 746-755
Cho, S. K., Moon, H. J., Kim, C. J., 2003. Journal of Microelectromechanical Systems 12, 70-80.
Cho, Y. H., Yamamoto, T., Sakai, Y., Fujii, T., Kim, B., 2006. Journal of Microelectromechanical Systems 15, 287-295
Curtis, T. M., Widder, M. W., Brennan, L. M., Schwager, S. J., van der Schalie, W. H., Fey, J., Salazar, N., 2009. Lab on a Chip 9, 2176-2183
DePaola, N., Phelps, J. E., Florez, L., Keese, C. R., Minnear, F. L., Giaever, I., Vincent, P., 2001. Ann Biomed Eng 29, 648-656
Dharmasiri, U., Balamurugan, S., Adams, A. A., Okagbare, P. I., Obubuafo, A., Soper, S. A., 2009. Electrophoresis 30, 3289-3300
Dharmasiri, U., Njoroge, S. K., Witek, M. A., Adebiyi, M. G., Kamande, J. W., Hupert, M. L., Barany, F., Soper, S. A., 2011. Analytical Chemistry 83, 2301-2309
Dive, C., Gregory, C. D., Phipps, D. J., Evans, D. L., Milner, A. E., Wyllie, A. H., 1992. Biochimica et Biophysica Acta 1133, 275-285
Eydelnant, I. A., Uddayasankar, U., Li, B., Liao, M. W., Wheeler, A. R., 2012. Lab on a Chip 12, 750-757
Fan, S. K., Huang, P. W., Wang, T. T., Peng, Y. H., 2008. Lab on a Chip 8, 1325-1331
Fiddes, L. K., Luk, V. N., Au, S. H., Ng, A. H. C., Luk, V. M., Kumacheva, E., Wheeler, A. R., 2012. Biomicrofluidics 6, 014112
Gawad, S., Cheung, K., Seger, U., Bertsch, A., Renaud, P., 2004. Lab on a Chip 4, 241-251
Giaever, I., Keese, C. R., 1991. Proc Natl Acad Sci USA 88, 7896-7900
Giaever, I., Keese, C. R., 1993. Nature 366, 591-592
Gray, D. S., Tan, J. L., Voldman, J., Chen, C. S., 2004. Biosens Bioelectron 19, 1765-1774
Hadwen, B., Broder, G. R., Morganti, D., Jacobs, A., Brown, C., Hector, J. R., Kubota, Y., Morgan, H., 2012. Lab on a Chip 12, 3305-3313
Han, A., Frazier, A. B., 2006. Lab on a Chip 6, 1412-1414
Han, A., Yang, L., Frazier, A. B., 2007. Clinical Cancer Research 13, 139-143
Han, K. H., Han, A., Frazier, A. B., 2006. Biosens Bioelectron 21, 1907-1914
Holmes, D., Pettigrew, D., Reccius, C. H., Gwyer, J. D., van Berkel, C., Holloway, J., Davies, D. E., Morgan, H., 2009. Lab Chip 9, 2881-2889
http://www.biophysics.com, Mar. 30, 2012. Applied Biophysics: Quantifying Cell Behaviour.
Ikeda, M., Kohno, M., Takeda, T., 1995. Hypertension 26, 401-405
James, C. D., Reuel, N., Lee, E. S., Davalos, R. V., Mani, S. S., Carroll-Portillo, A., Rebeil, R., Martino, A., Apblett, C. A., 2008. Biosens Bioelectron 23, 845-851
Jang, L. S., Wang, M. H., 2007. Biomedical Microdevices 9, 737-743
Keese, C. R., Bhawe, K., Wegener, J., Giaever, I., 2002. Biotechniques 33, 842-844
Keese, C. R., Wegener, J., Walker, S. R., Giaever, I., 2004. Proc Natl Acad Sci USA 101, 1554-1559
Kunas, K. T., Papoutsakis, E. T., 2009. Biotechnology and bioengineering 102, 980-987; discussion 977-989
Lippincott-Schwartz, J., 2011. Annu Rev Biochem 80, 327-332
Lo, C. M., Keese, C. R., Giaever, I., 1995. Biophys J 69, 2800-2807
Lundien, M. C., Mohammed, K. A., Nasreen, N., Tepper, R. S., Hardwick, J. A., Sanders, K. L., Van Horn, R. D., Antony, V. B., 2002. J Clin Immunol 22, 144-152

Mengual Gomez, D. L., Belaich, M. N., Rodriguez, V. A., Ghiringhelli, P. D., 2010. BMC Biotechnol 10, 68

Mishra, N. N., Retterer, S., Zieziulewicz, T. J., Isaacson, M., Szarowski, D., Mousseau, D. E., Lawrence, D. A., Turner, J. N., 2005. Biosens Bioelectron 21, 696-704

Morgan, H., Sun, T., Holmes, D., Gawad, S., Green, N. G., 2007. J. Phys. D: Appl. Phys. 40, 61-70

Otto, A. M., Brischwein, M., Niendorf, A., Henning, T., Motrescu, E., Wolf, B., 2003. Cancer Detect Prev 27, 291-296

Rumenapp, C., Remm, M., Wolf, B., Gleich, B., 2009. Biosens Bioelectron 24, 2915-2919

Shah, G. J., Ohta, A. T., Chiou, E. P., Wu, M. C., Kim, C. J., 2009. Lab on a Chip 9, 1732-1739

Shah, G. J., Veale, J. L., Korin, Y., Reed, E. F., Gritsch, H. A., Kim, C. J., 2010. Biomicrofluidics 4, 44106

Shih, S. C. C., Fobel, R., Kumar, P., Wheeler, A. R., 2011. Lab on a Chip 11, 535-540

Shih, S. C. C., Yang, H., Jebrail, M. J., Fobel, R., McIntosh, N., Al-Dirbashi, O. Y., Chakraborty, P., Wheeler, A. R., 2012. Analytical Chemistry 84, 3731-3738

Sohn, L. L., Saleh, O. A., Facer, G. R., Beavis, A. J., Allan, R. S., Notterman, D. A., 2000. Proc Natl Acad Sci USA 97, 10687-10690

Srigunapalan, S., Eydelnant, I. A., Simmons, C. A., Wheeler, A. R., 2012. Lab on a Chip 12, 369-375

Stolwijk, J. A., Hartmann, C., Balani, P., Albermann, S., Keese, C. R., Giaever, I., Wegener, J., 2011. Biosens Bioelectron 26, 4720-4727

Sun, T., Morgan, H., 2010. Microfluid Nanofluid 8, 423-443

Sun, T., Swindle, E. J., Collins, J. E., Holloway, J. A., Davies, D. E., Morgan, H., 2010. Lab on a Chip 10, 1611-1617

Sun, T., van Berkel, C., Green, N. G., Morgan, H., 2009. Microfluid Nanofluid 6, 179-187

Taff, B. M., Voldman, J., 2005. Analytical Chemistry 77, 7976-7983

Thein, M., Asphahani, F., Cheng, A., Buckmaster, R., Zhang, M., Xu, J., 2010. Biosens Bioelectron 25, 1963-1969

Tiruppathi, C., Malik, A. B., Del Vecchio, P. J., Keese, C. R., Giaever, I., 1992. Proc Natl Acad Sci USA 89, 7919-7923

Vergauwe, N., Witters, D., Ceyssens, F., Vermeir, S., Verbruggen, B., Puers, R., Lammertyn, J., 2011. Journal of Micromechanics and Microengineering 21

Wang, L., Zhu, J., Deng, C., Xing, W. L., Cheng, J., 2008. Lab on a Chip 8, 872-878

Wegener, J., Sieber, M., Galla, H. J., 1996. J Biochem Biophys Methods 32, 151-170

Weinlich, M., Heydasch, U., Mooren, F., Starlinger, M., 1998. Res Exp Med (Berl) 198, 73-82

Wheeler, A. R., 2008. Science 322, 539-540

Witters, D., Vergauwe, N., Vermeir, S., Ceyssens, F., Liekens, S., Puers, R., Lammertyn, J., 2011. Lab on a Chip 11, 2790-2794

Zudaire, E., Cuesta, N., Murty, V., Woodson, K., Adams, L., Gonzalez, N., Martinez, A., Narayan, G., Kirsch, I., Franklin, W., Hirsch, F., Birrer, M., Cuttitta, F., 2008. Journal of Clinical Investigation 118, 640-650

Therefore what is claimed is:

1. A digital microfluidic device comprising:
    a first plate comprising:
        a first insulating substrate;
        an array of discrete electrodes formed on said first insulating substrate;
        a first dielectric layer provided on said discrete electrodes, wherein a surface of said first dielectric layer is hydrophobic;
    a second plate comprising:
        a second insulating substrate;
        at least one reference electrode formed on said second insulating substrate; and
        a second dielectric layer provided on said reference electrode, wherein a surface of said second dielectric layer is hydrophobic;
    wherein said second plate is provided in a spaced relationship relative to said first plate, such that a droplet contacting said first plate and said second plate is transportable among locations associated with said discrete electrodes under application of a suitable bias between said discrete electrodes and said reference electrode;
    wherein at least one of said first plate and said second plate comprises a locally hydrophilic surface region that is proximal to a pre-selected discrete electrode of said array of discrete electrodes, wherein said locally hydrophilic surface region is configured for attachment of adherent cells; and
    wherein at least one of said first plate and said second plate further comprises a dedicated sensing electrode that is proximal to said locally hydrophilic surface region;
    wherein a droplet is transportable to said locally hydrophilic surface region based on the application of a voltage between said array of discrete electrodes and said reference electrode in the absence of actuation of said dedicated sensing electrode, and wherein an electrical signal associated with an impedance of adherent cells attached to said locally hydrophilic surface region is measurable based on another voltage applied between said dedicated sensing electrode and one of said pre-selected discrete electrode and said reference electrode.

2. The digital microfluidic device according to claim 1 wherein a surface of said dedicated sensing electrode is uncoated.

3. The digital microfluidic device according to claim 1 wherein said dedicated sensing electrode is formed on said first insulating substrate, and wherein said at least a portion of said dedicated sensing electrode is surrounded by at least a portion of said pre-selected discrete electrode.

4. The digital microfluidic device according to claim 1 wherein said dedicated sensing electrode is formed on said first dielectric layer.

5. The digital microfluidic device according to claim 1 wherein said dedicated sensing electrode is formed on said second insulating substrate, and wherein said at least a portion of said dedicated sensing electrode is surrounded by at least a portion of said reference electrode.

6. The digital microfluidic device according to claim 1 wherein at least one of said first dielectric layer and said second dielectric layer has a locally reduced thickness over said dedicated sensing electrode.

7. The digital microfluidic device according to claim 6 wherein said locally reduced thickness is less than approximately 5 microns.

8. A method of measuring an electrical signal associated with the presence of adherent cells on a digital microfluidic device, the method comprising:
    providing a digital microfluidic device according to claim 1,
    electrically actuating the digital microfluidic device to transport a droplet of low-conductivity medium to the pre-selected discrete electrode, wherein the electrical conductivity of the low-conductivity medium is lower than the electrical conductivity of the cell culture medium;

electrically actuating the digital microfluidic device to passively dispense a sub-droplet of the low-conductivity medium, thereby displacing the droplet of cell culture medium; and applying an AC voltage between the dedicated sensing electrode and one of said discrete electrode and said reference electrode and measuring an electrical signal associated with the impedance of the adherent cells.

9. The method according to claim 8 wherein the AC voltage is applied with a frequency exceeding a pre-selected frequency threshold.

10. The method according to claim 9 wherein the pre-selected frequency threshold is selected to obtain a pre-selected detection sensitivity.

11. The method according to claim 9 wherein the pre-selected frequency threshold is greater than approximately 10 kHz.

12. The method according to claim 9 wherein the pre-selected frequency threshold is greater than approximately 15 kHz.

13. The method according to claim 8 wherein the low-conductivity medium is approximately isotonic.

14. The method according to claim 8 wherein the low-conductivity medium comprises sucrose.

15. The method according to claim 8 wherein the low-conductivity medium comprises a sucrose concentration of approximately 500 mM.

16. The method according to claim 8 wherein said droplet of cell culture medium is a sub-droplet that is provided by passive dispensing.

17. The method according to claim 8 further comprising:

providing an additional droplet of cell culture medium on said digital microfluidic device; and electrically actuating the digital microfluidic device to transport the additional droplet of cell culture medium to the pre-selected discrete electrode; and electrically actuating the digital microfluidic device to passively dispense a sub-droplet of cell culture medium, thereby displacing the sub-droplet of low-conductivity medium.

18. The method according to claim 17 further comprising culturing the adherent cells in the sub-droplet of cell culture medium.

19. The method according to claim 8 wherein the electrical signal is proportional to an impedance of the adherent cells.

20. The method according to claim 8 wherein further comprising relating the measured electrical signal to a density of cells attached to said locally hydrophilic surface region.

21. The method according to claim 8 wherein further comprising relating the measured electrical signal to a quantity of cells attached to said locally hydrophilic surface region.

* * * * *